US012746013B2

(12) United States Patent
Tetzlaff et al.

(10) Patent No.: US 12,746,013 B2
(45) Date of Patent: Sep. 29, 2026

(54) MEDICAL TOOL WITH VIBRATION DAMPING

(71) Applicant: INSURGICAL, INC., Austin, TX (US)

(72) Inventors: Philip Tetzlaff, Austin, TX (US); Richard Acevedo, Austin, TX (US); Aaron Jon Fowler, Leander, TX (US)

(73) Assignee: INSURGICAL, INC., Austin, TX (US)

( * ) Notice: Subject to any disclaimer, the term of this patent is extended or adjusted under 35 U.S.C. 154(b) by 280 days.

(21) Appl. No.: 18/506,312

(22) Filed: Nov. 10, 2023

(65) Prior Publication Data

US 2024/0164791 A1 May 23, 2024

Related U.S. Application Data

(60) Provisional application No. 63/426,659, filed on Nov. 18, 2022.

(51) Int. Cl.
*A61B 17/14* (2006.01)

(52) U.S. Cl.
CPC .................................. *A61B 17/142* (2016.11)

(58) Field of Classification Search
CPC ..... A61B 17/14; A61B 17/142; A61B 17/144; B23D 51/16; B23D 51/1615; B23Q 5/02; B23Q 5/04; B23Q 5/043; B23Q 5/045; B24B 23/04; B25F 5/006; B25F 5/02
See application file for complete search history.

(56) References Cited

U.S. PATENT DOCUMENTS 5,263,972 A * 11/1993 Evans .................... B23D 51/10 606/176
5,697,158 A * 12/1997 Klinzing ............ B23D 57/0076 30/340
5,813,477 A * 9/1998 Clay .................... B25D 17/043 267/140
6,099,397 A 8/2000 Wurst
6,318,479 B1 * 11/2001 Giardino ................. B25B 21/02 173/162.1
6,321,853 B2 * 11/2001 Giardino ................. B25B 21/02 173/1
6,810,970 B1 * 11/2004 Kraenzler ................. B25F 5/02 173/217

(Continued)

FOREIGN PATENT DOCUMENTS

EP 2452785 A2 * 5/2012 .............. B25F 5/006
EP 2625006 B1 * 12/2016 ................ B25F 5/00

(Continued)

OTHER PUBLICATIONS

International Search Authority, International Search Report and Written Opinion dated Feb. 28, 2024 in International Application No. PCT/US23/37129 (10 pages).

*Primary Examiner* — Eric S Gibson
(74) *Attorney, Agent, or Firm* — Trop, Pruner & Hu, P.C.

(57) ABSTRACT

A battery-powered tool equipped with damping to reduce vibration, noise and heat generated by drive components and high oscillation rates of components and mating accessories mounted to those tools. Some versions of the tool may include elastomeric damping pads, rings, strips, blocks, threaded mounts or co-molded elements. Other versions may include shrouded components or shrouds comprising elastomeric materials.

18 Claims, 15 Drawing Sheets

(56) References Cited

U.S. PATENT DOCUMENTS

| | | | | |
|---|---|---|---|---|
| 7,497,860 | B2 * | 3/2009 | Carusillo | A61B 17/142 606/86 R |
| 8,100,912 | B2 * | 1/2012 | Marietta | A61B 17/142 606/176 |
| 8,205,683 | B2 * | 6/2012 | Schadow | B25F 5/006 173/162.1 |
| 9,461,281 | B2 * | 10/2016 | Wackwitz | H01M 10/0525 |
| 10,105,149 | B2 * | 10/2018 | Haider | A61B 17/17 |
| 10,213,852 | B2 * | 2/2019 | Qian | B27B 19/006 |
| 11,045,939 | B2 * | 6/2021 | Kotsuji | B27B 19/006 |
| 11,529,163 | B2 * | 12/2022 | Stritch | A61B 17/320758 |
| 12,021,437 | B2 * | 6/2024 | Duncan | B25F 5/006 |
| 2001/0000882 | A1 * | 5/2001 | Giardino | B25F 5/006 173/210 |
| 2006/0009796 | A1 * | 1/2006 | Carusillo | A61B 17/157 606/178 |
| 2009/0326540 | A1 * | 12/2009 | Estes | B23B 31/10741 279/78 |
| 2010/0193209 | A1 * | 8/2010 | Schadow | B24B 23/04 173/217 |
| 2012/0118599 | A1 * | 5/2012 | Schadow | B25F 5/006 173/162.2 |
| 2012/0129435 | A1 * | 5/2012 | Ikuta | B25F 5/006 451/358 |
| 2013/0196203 | A1 * | 8/2013 | Wackwitz | H01M 10/0525 429/96 |
| 2013/0209017 | A1 * | 8/2013 | Schadow | B24B 41/007 267/141 |
| 2013/0304069 | A1 * | 11/2013 | Bono | A61B 17/1671 606/80 |
| 2014/0124230 | A1 | 5/2014 | Johnson | |
| 2016/0022374 | A1 * | 1/2016 | Haider | A61B 17/142 606/96 |
| 2016/0271711 | A1 * | 9/2016 | Qian | B25F 5/001 |
| 2017/0334056 | A1 | 11/2017 | Makita | |
| 2018/0029215 | A1 * | 2/2018 | Zhong | B25F 5/006 |
| 2018/0319001 | A1 * | 11/2018 | Zhong | B25F 5/006 |
| 2019/0099873 | A1 * | 4/2019 | Zhang | H02K 7/145 |
| 2019/0290297 | A1 * | 9/2019 | Haider | A61B 34/20 |
| 2019/0298404 | A1 * | 10/2019 | Stritch | A61B 17/320068 |
| 2019/0299387 | A1 * | 10/2019 | Kotsuji | B25F 5/02 |
| 2020/0178998 | A1 * | 6/2020 | Behzadi | A61B 17/1675 |
| 2020/0197027 | A1 * | 6/2020 | Hershberger | A61B 17/1628 |
| 2021/0086276 | A1 * | 3/2021 | Ling | B25D 17/24 |
| 2022/0273315 | A1 * | 9/2022 | Viola | A61B 17/157 |
| 2023/0202020 | A1 * | 6/2023 | Fukinuki | B24B 23/04 173/199 |
| 2023/0246516 | A1 * | 8/2023 | Duncan | B25F 5/02 173/162.1 |
| 2023/0263534 | A1 * | 8/2023 | Kowall | A61B 17/142 606/176 |
| 2023/0302620 | A1 * | 9/2023 | Dubnicka | B25F 5/001 |
| 2023/0373074 | A1 * | 11/2023 | Zimmermann | B25F 5/006 |
| 2023/0405790 | A1 * | 12/2023 | Lottes | B25B 21/02 |
| 2024/0164791 | A1 * | 5/2024 | Tetzlaff | A61B 17/142 |
| 2024/0366325 | A1 * | 11/2024 | Gonzalez Chapa | A61B 34/30 |
| 2025/0033180 | A1 * | 1/2025 | Iseda | B23D 49/16 |

FOREIGN PATENT DOCUMENTS

| | | | | | |
|---|---|---|---|---|---|
| EP | 3403771 | A1 * | 11/2018 | | B25F 3/00 |
| WO | WO-9722303 | A1 * | 6/1997 | | A61B 17/142 |
| WO | WO-02051596 | A2 * | 7/2002 | | B25B 21/02 |
| WO | WO-2014144780 | A1 * | 9/2014 | | A61B 90/13 |
| WO | WO-2018226945 | A1 * | 12/2018 | | A61B 17/1628 |
| WO | WO-2012048240 | A2 * | 4/2021 | | B25F 5/00 |
| WO | WO-2022020678 | A2 * | 1/2022 | | A61B 17/142 |
| WO | WO-2022261302 | A1 * | 12/2022 | | H02K 7/145 |
| WO | WO-2023101022 | A1 * | 6/2023 | | B23D 49/162 |
| WO | WO-2023141644 | A2 * | 7/2023 | | B25J 15/04 |
| WO | WO-2024107385 | A1 * | 5/2024 | | F16F 15/08 |

* cited by examiner

MEDICAL TOOL WITH VIBRATION DAMPING

CROSS-REFERENCE TO RELATED APPLICATIONS

This application claims the benefit of U.S. Prov. App. No. 63/426,659 titled "MEDICAL TOOL WITH VIBRATION DAMPING" filed Nov. 18, 2022. The provisional application is incorporated by reference herein as if reproduced in full below.

BACKGROUND

The present disclosure is directed to battery-powered surgical hand tools, and more particularly to battery-powered tools equipped with damping to reduce vibration, noise and wear generated by offset drive components and high oscillation rates of mating accessories mounted to those tools, particularly seen in oscillating or reciprocating surgical saws.

Vibration is one of the principle causes of wear and degradation of tool components. Further, said vibration can be transmitted to the hand of the user, generating discomfort during use.

Additionally, said vibration may also translate into unacceptable noise levels within the operating theater, causing distraction.

Finally, excessive vibration may also generate friction, another source of degradation of tool components.

SUMMARY

Power tools, including battery-powered surgical tools and saws have been reported to generate vibration and noise in the user's hand during use in the operating room. For example, the vibration (and noise) from a surgical saw for example, is most often generated due to the offset nature of the blade mass of an oscillating saw operating at a very high rate of speed. Any components not held in direct contact, have the potential to generate noise when vibrating against each other due to offset mechanism and mass imbalances. The acceleration of this offset mass also generates the vibration of the device in the hand of the user. Additionally, wear can be generated due to excessive loading or use of the device but can also be generated by the friction of vibrating elements against each other. This may be noted between components in the device, or around joints or seams in the device assembly, near screws on the surface of an external housing.

Vibration is typically transmitted from the source, through the housing, down into and through the handle, and may ultimately be transmitted to the battery compartment of the tool housing. This vibration can cause wear to occur when mechanical elements vibrate against each other. Resulting vibration can cause the assembly seams to vibrate against each other and generate wear, and can generate visible wear of device components, such as in the internal battery housing, where the battery and surface edges between the battery compartment and saw housing interface. Additionally, vibration can also result in damage to the electrical contacts of the battery when in the housing.

Excessive noise generation during use is also reported. This noise can be a distraction in the operating room and perceived as uncomfortable for the user.

One potential source of wear has been tracked back to the (excessive) vibration, caused by oscillation or reciprocation of a saw blade driven by an axially offset shaft of the saw, which is then coupled to the drive motor.

To address these issues, the present disclosure illustrates and describes a number of design modification improvements incorporated into the support structures, housing and drive mechanisms to reduce the vibration and ultimately, noise and wear generation commonly seen in these types of devices including; adding elastomer supports between the support bearing of the offset shaft and device housing; adding elastomer mounts, strips, or end cap vibration dampers on front and/or back (or both) ends of the drive motor; adding elastomeric damping mounts, strips or internal sheathing to the internal surfaces of the drive shaft and bearing shroud covering the drive shaft and bearing(s) within the proximal saw housing; bonding assembly seams (glue, ultrasonic welding, heat staking) in the handle during final assembly of the exterior housing assembly, to reduce potential for vibration of components against each other when in use; design of drive components to reduce coupling vibrations and wear generation caused at drive motor speeds; and generate an Encased Hybrid Drive Shaft Assembly by completely encasing the entire drive assembly in a "stiff" elastomeric housing that fits within the outer external saw housing.

Among the unanticipated discoveries and benefits of these design developments was a reduction in the oscillation or reciprocation and "jump" in the cutting edge of the saw blade, due to a more flexible fork connection in the pivot link/pivot shaft interface. Further a significant reduction in noise and wear generation was seen as a result of strategic choice and placement of elastomeric damping materials as well as from shrouding of key drive components with elastomeric materials. Benefits of these design modifications can also be applied to other powered tools such as reciprocating and oscillating saws, (medical or commercial); and automated impactors such as broach drivers and osteotomes, to name just a few.

Provided herein is a modular system comprising a limited-use, rechargeable, or disposable battery-operated orthopedic hand tool having modular internal components; said modular internal components comprising: a variable speed motor providing a rotational output; an internal drive mechanism comprising; a first drive shaft; a motor shaft coupling; an offset shaft; and at least one drive shaft bearing; one or more elastomeric dampers; an external housing comprising a handle grip; a trigger mechanism to control the variable speed motor; a trigger control processor, a rechargeable battery; and a battery compartment.

In some embodiments, the system further comprises: an elastomeric damper fitted about a support of the offset shaft; wherein the damper could be placed; around a support bearing or bearings; about the sides of the support bearing or bearings; around the support bearing and variable speed motor; or anywhere around the exterior of the support bearings and variable speed motor and within the external housing.

In some embodiments, the system further comprises: an elastomeric damper fitted about the variable speed motor; wherein the damper could be placed about; a posterior end thereof; an anterior end thereof; both the anterior and posterior end thereof, or anywhere around the exterior of the variable speed motor.

In some embodiments, the system further comprises a drive mechanism shroud surrounding the internal drive mechanism.

In some embodiments of the system, the drive mechanism shroud internally comprises one or more elastomeric dampers having a durometer between Shore A 60-100 or between Shore D 0-60.

In some embodiments of the system, the drive mechanism shroud externally comprises one or more elastomeric dampers having a durometer between Shore A 60-100 or between Shore D 0-60.

In some embodiments, the system further comprises one or more elastomeric dampers having a durometer between Shore A 40-100 in the battery compartment.

In some embodiments, the system further comprises: a second drive shaft configured at a different orientation (e.g.: 90°) to the offset shaft; at least one bearing on the second drive shaft; and an attachment receiver coupled to the second drive shaft for modular attachments used for performing surgical procedures; wherein the second drive shaft and the at least one bearing on the second drive shaft further comprise elastomeric damping features.

In some embodiments of the system, the drive mechanism comprises one or more elastomeric dampers having a durometer between Shore A 60-100 or between Shore D 0-60 about or around the first drive shaft, the first output shaft, the second drive shaft, the second output shaft, all of the bearings and the motor.

In some embodiments of the system, the variable speed motor is configurable to drive the second drive shaft in a working range between 8,500-10,500 oscillations per minute (OPM). In some embodiments of the system, the variable speed motor is configurable to drive the second drive shaft in a working range between 7,000-14,000 oscillations per minute (OPM).

In some embodiments of the system, the variable speed motor is configurable to drive the second drive shaft in a range between 0-16,000 oscillations per minute (OPM).

In some embodiments of the system, the variable speed motor is configurable to drive the second drive shaft in a range between 0-18,000 oscillations per minute (OPM).

In some embodiments of the system, the elastomeric dampers maintain a sound level of 80-90 dB or less when the system is running.

In some embodiments of the system, the elastomeric dampers decrease the amplitude of vibration by 10%-20%.

In some embodiments of the system, the elastomeric dampers decrease the amplitude of vibration by 20% to 30%.

In some embodiments, the system further comprises a counterbalance weight within the external housing to balance the weight of the modular system in a user's hand.

Provided herein is a modular medical device system comprising a limited-use, rechargeable, or disposable, battery-operated orthopedic hand saw having modular internal components; said modular internal components comprising: a variable speed motor providing a rotational output; an internal drive mechanism comprising; a first drive shaft; a motor shaft coupling; an offset shaft; at least one drive shaft bearing; a second drive shaft configured at a different orientation (e.g.: 90°) to the offset shaft; at least one bearing on the second drive shaft; one or more elastomeric dampers; and an external housing; wherein the internal drive mechanism, the second drive shaft and the at least one bearing on the second drive shaft are encased in a shroud; and wherein the encasing shroud is fitted within the external housing.

In some embodiments of the modular medical device system, the encasing shroud is further coupled to the proximal end of the variable speed motor.

In some embodiments, the modular medical device system further comprises an elastomeric damper fitted about the posterior end of the variable speed motor, or about the exterior of the encasing shroud, or both.

In some embodiments of the modular medical device system, the variable speed motor is configurable to drive the second drive shaft in a working range between 8,500-10,500 oscillations per minute (OPM).

In some embodiments of the modular medical device system, the variable speed motor is configurable to drive the second drive shaft in a working range between 7,000-14,000 oscillations per minute (OPM).

In some embodiments of the system, the variable speed motor is configurable to drive the second drive shaft in a range between 0-16,000 oscillations per minute (OPM).

In some embodiments of the system, the variable speed motor is configurable to drive the second drive shaft in a range between 0-18,000 oscillations per minute (OPM).

In some embodiments of the modular medical device system, the elastomeric dampers maintain a sound level of 80-90 dB or less for the orthopedic hand saw when the system is running.

In some embodiments of the modular medical device system, the elastomeric dampers decrease the amplitude of vibration from un-damped systems by 10%-30%, detectable in the external housing when the system is running with a cutting blade installed.

In some embodiments, the modular medical device system further comprises: a handle grip on the external housing and assembly features making the external housing and handle grip removable and replaceable; a trigger mechanism to control the variable speed motor; a trigger control processor, a rechargeable battery; a battery compartment.

In some embodiments of the modular medical device system, the internal shroud comprises an elastomeric material configured to reduce or absorb vibration by 10%-30% from un-damped systems, detectable in the external housing when the system is running, with a cutting blade installed.

In some embodiments, the modular medical device system further comprises a counterbalance weight within the housing of the system to balance the weight of the modular system in a user's hand.

In some embodiments, the modular medical device system further comprises an attachment receiver coupled to the second drive shaft for receiving and capturing modular attachments used for performing surgical procedures.

In some embodiments of the modular medical device system, the attachment receiver is configured to receive and capture saw blades or similar cutting attachments.

In any one of the embodiments, described herein, the motor, the internal drive mechanism, the internal shroud, the external housing comprising the handle grip, the trigger mechanism and the attachment receiver are configurable as modular components.

In any one of the embodiments, described herein, the addition of elastomeric dampers, or a drive mechanism shroud, or a drive mechanism shroud comprising elastomeric damping materials added to the system to reduce vibration, will also result in the reduction of wear of system components.

Provided here is a medical power tool comprising: a modular, limited-use, rechargeable, or disposable, battery-operated orthopedic hand tool having modular internal components; said modular internal components comprising: a variable speed motor providing a rotational output; an internal drive mechanism comprising; a first drive shaft; a motor shaft coupling; an offset shaft; and at least one drive shaft bearing; one or more elastomeric dampers placed about the internal drive mechanism; a modular, removable external housing comprising a handle grip; a trigger mechanism to control the variable speed motor; a trigger control processor, a rechargeable battery; and a battery compartment.

In some embodiments, the medical power tool further comprises one or more additional elastomeric dampers fitted about the variable speed motor; wherein the one or more dampers are placed about; a posterior end thereof; an anterior end thereof; both the anterior and posterior end thereof, or anywhere around the exterior of the variable speed motor.

In some embodiments, the medical power tool further comprises a shroud surrounding the internal drive mechanism.

In some embodiments of the medical power tool, the drive mechanism shroud internally comprises elastomeric dampers having a durometer between Shore A 60-100 or between Shore D0-60.

In some embodiments of the medical power tool, the drive mechanism shroud externally comprises elastomeric dampers having a durometer between Shore A 60-100 or between Shore D0-60.

In some embodiments of the medical power tool, the drive mechanism shroud comprises elastomeric properties having a durometer between Shore A 60-100 or between Shore D 0-60.

In some embodiments, the medical power tool further comprises one or more additional elastomeric dampers having a durometer between Shore A 40-100 in the battery compartment.

In some embodiments, the medical power tool further comprises a second drive shaft configured at a different orientation (e.g.: 90°) to the offset shaft; at least one bearing on the second drive shaft; and an attachment receiver coupled to the second drive shaft configured to receive and capture modular attachments used for performing surgical procedures.

In some embodiments, the medical power tool further comprises a counterbalance weight within the external housing to balance the weight of the power tool in a user's hand.

In some embodiments of the medical power tool, the variable speed motor is configurable to drive the second drive shaft in a range between 8,500-10,500 oscillations per minute (OPM).

In some embodiments of the modular medical device system, the variable speed motor is configurable to drive the second drive shaft in a working range between 7,000-14,000 oscillations per minute (OPM).

In some embodiments of the system, the variable speed motor is configurable to drive the second drive shaft in a range between 0-16,000 oscillations per minute (OPM).

In some embodiments of the system, the variable speed motor is configurable to drive the second drive shaft in a range between 0-18,000 oscillations per minute (OPM).

In some embodiments of the medical power tool, the elastomeric dampers maintain a sound level of 80-90 dB or less when the system is running.

In some embodiments of the medical power tool, the shroud elastomeric dampers maintain a sound level of 80-90 dB or less when the system is running.

In some embodiments of the medical power tool, the elastomeric dampers maintain a sound level of 80-90 dB or less when the system is running.

In some embodiments of the medical power tool, the elastomeric dampers decrease the amplitude of vibration by 10%-30% when the system is running with a cutting blade installed.

In any one of the power tool embodiments, described herein, the addition of elastomeric dampers, or a drive mechanism shroud, or a drive mechanism shroud comprising elastomeric damping materials added to the system to reduce vibration, will also result in the reduction of wear.

Provided herein is a battery-operated surgical saw comprising: a modular, limited-use, rechargeable or disposable orthopedic hand tool having modular internal components; said modular internal components comprising: a variable speed motor providing a rotational output; an internal drive mechanism comprising; a first drive shaft; a motor shaft coupling; an offset shaft; and at least one drive shaft bearing; one or more elastomeric dampers; a modular, removable external housing comprising a handle grip; a trigger mechanism to control the motor; a trigger control processor, a rechargeable battery; and a battery compartment.

In some embodiments, the battery-operated surgical saw further comprises one or more elastomeric damper fitted about the variable speed motor; wherein said dampers are placed about; a posterior end; an anterior end; both the anterior and posterior end, or anywhere around the exterior of the variable speed motor.

In some embodiments, the battery-operated surgical saw further comprises a shroud surrounding the internal drive mechanism within the external housing.

In some embodiments of the battery-operated surgical saw, the drive mechanism shroud is optionally configured to: encase at least ½ of the variable speed motor, encase the internal drive mechanism and encase the extended pivot link mechanism in a single casing.

Alternately, in some embodiments of the battery-operated surgical saw, the drive mechanism shroud is optionally configured to: encase at least ½ of the variable speed motor and the internal drive mechanism in an attachable sub-casing and the extended pivot link in an attachable sub-casing.

In some embodiments, the shroud encases the entire variable speed motor, the internal drive mechanism and the extended pivot link mechanism in a single shroud casing.

In some embodiments of the battery-operated surgical saw, the drive mechanism shroud internally comprises one or more additional elastomeric dampers having a durometer between Shore A 60-100 or between Shore D 0-60.

In some embodiments of the battery-operated surgical saw, the drive mechanism shroud externally comprises one or more additional elastomeric dampers having a durometer between Shore A 60-100 or between Shore D 0-60.

In some embodiments of the battery-operated surgical saw, the drive mechanism shroud is comprised of a material comprising elastomeric properties having a durometer between Shore A 60-100 or between Shore D 0-60.

In some embodiments, the battery-operated surgical saw further comprises elastomeric dampers having a durometer between Shore A 40-100 in the battery compartment.

In some embodiments, the battery-operated surgical saw further comprises a second drive shaft configured at a different orientation to the offset shaft; at least one bearing on the second drive shaft; and an attachment receiver coupled to the second drive shaft configured to receive and capture modular attachments used for performing surgical procedures.

In some embodiments, the battery-operated surgical saw further comprises a counterbalance weight within the housing of the system to balance the weight of the modular system in a user's hand.

In some embodiments of the battery-operated surgical saw, the variable speed motor is configurable to drive the second drive shaft in a working range between 8,500-10,500 oscillations per minute (OPM).

In some embodiments of the modular medical device system, the variable speed motor is configurable to drive the second drive shaft in a working range between 7,000-14,000 oscillations per minute (OPM).

In some embodiments of the system, the variable speed motor is configurable to drive the second drive shaft in a range between 0-16,000 oscillations per minute (OPM).

In some embodiments of the system, the variable speed motor is configurable to drive the second drive shaft in a range between 0-18,000 oscillations per minute (OPM).

In some embodiments of the battery-operated surgical saw, the elastomeric dampers maintain a sound level of 80-90 dB or less when the system is running.

In some embodiments of the battery-operated surgical saw, the one or more additional elastomeric dampers maintain a sound level of 80-90 dB or less when the system is running.

In some embodiments of the battery-operated surgical saw, the drive mechanism shroud maintains a sound level of 80-90 dB or less when the system is running.

In some embodiments of the battery-operated surgical saw, the elastomeric dampers decrease the amplitude of vibration by 10%-30% when the system is running with a cutting blade installed.

In any embodiment of the battery-operated surgical saw described herein, the addition of elastomeric dampers, or a drive mechanism shroud, or a drive mechanism shroud comprising elastomeric damping materials added to the system to reduce vibration, will also result in the reduction of wear.

In other optional embodiments, the addition of elastomeric dampers, or a drive mechanism shroud, or a drive mechanism shroud comprising elastomeric damping materials can also be applied to other powered tools such as reciprocating and oscillating saws, (medical or commercial) to reduce vibration and noise.

Optionally, in still further embodiments, the addition of elastomeric dampers, or a drive mechanism shroud, or a drive mechanism shroud comprising elastomeric damping materials can also be applied to other powered tools such as reciprocating saws, automated impactors, broach drivers and osteotomes, (medical or commercial), to name just a few, to reduce vibration.

In further optional embodiments, or in any embodiment of an alternative tool described herein, the addition of elastomeric dampers, or a drive mechanism shroud, or a drive mechanism shroud comprising elastomeric damping materials added to the system to reduce vibration, will also result in the reduction of heat generation and radiated heat felt in the hand of a user.

Additional aspects and advantages of the present disclosure will become readily apparent to those skilled in this art from the following detailed description, wherein only exemplary embodiments of the present disclosure are shown and described, simply by way of illustration of the several modes or best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 1:
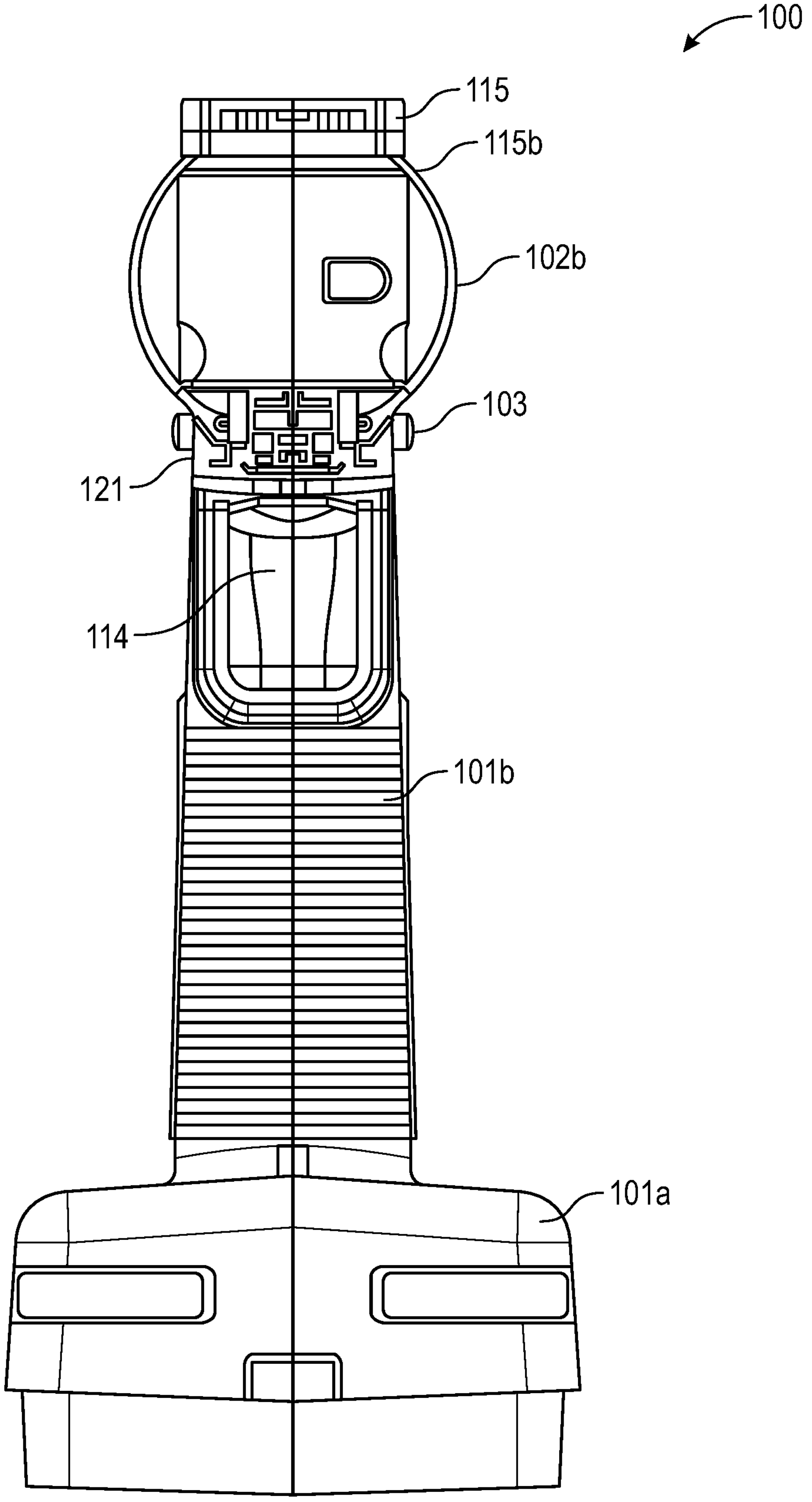
FIG. 1 is a front view of a battery-operated orthopedic hand tool saw having modular internal components with an electro-mechanical drive motor, an offset shaft drive coupling, an offset shaft, short fork shaft and gear drive shaft.

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Power tools, such as battery-powered surgical saws have been reported to generate vibration and excessive noise in the user's hand during use in the operating room. For example, the vibration (and noise) from a surgical saw for example, is most often generated due to the offset nature of the blade mass of an oscillating saw operating at a very high rate of speed. Any components not held in direct contact, have the potential to generate noise when vibrating against each other due to offset shaft imbalances. The acceleration of this offset mass also generates the vibration of the device in the hand of the user. Additionally, wear can occur due to excessive loading or use of the device but can also be generated by the friction of vibrating elements against each other. This may be noted around joints or seams in the device assembly, and near screws on the surface of an external housing.

Vibration is typically transmitted from the source, through the housing, down into and through the handle, and may ultimately be transmitted to the battery compartment of the tool housing. This vibration is commonly at a frequency (9,000 to 12,000 oscillations per minute (OPM)) and amplitude (in excess of 100 m/s^2) which can cause damage to occur when mechanical elements vibrate against each other. Resulting vibration can cause the assembly seams to vibrate against each other and can generate visible wear of device components, such as in the internal battery housing, where the battery and surface edges between the battery compartment and saw housing interface. Additionally, vibration can result in damage to the electrical contacts of the battery when in the housing.

To address these issues, the present disclosure illustrates and describes a number of design modification improvements incorporated into the support structures, housing and drive mechanisms of surgical saws to reduce the vibration and ultimately, noise and wear commonly seen in these types of devices including; adding elastomer supports between the support bearing of the offset shaft and device housing; adding elastomer mounts, strips, or end cap vibration dampers on front and/or back (or both) ends of the drive motor; adding elastomeric damping mounts, strips or internal sheathing to the internal surfaces of the drive shaft and bearing shroud covering the drive shaft and bearing(s) within the proximal saw housing; bonding assembly seams (glue, ultrasonic welding, heat staking) in the handle during final assembly of the exterior housing assembly, to reduce potential for vibration of components against each other when in use; design drive components to minimize coupling vibrations and wear caused at high drive motor speeds; and generate an Encased Hybrid Drive Shaft Assembly by completely encasing the entire drive assembly in a "stiff" housing that fits within the outer external saw housing.

Benefits of these design modifications can also be applied to other powered tools such as reciprocating and oscillating saws, (medical or commercial); and automated impactors such as broach drivers and osteotomes, to name just a few.

In particular, the design improvements described herein are particularly beneficial not only to reusable surgical saws, but also when applied to limited-use tools that may be designed for refurbishment after some set limited number of uses, or any single-use power tool.

Definitions as Used Herein

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 40.0 mm, 30.0 mm, 20.0 mm, 10.0 mm 5.0 mm 1.0 mm, 0.9 mm, 0.8 mm, 0.7 mm, 0.6 mm, 0.5 mm, 0.4 mm, 0.3 mm, 0.2 mm or 0.1 mm of a given value or range. In certain embodiments, the term "about" or "approximately" means within 5.0 kg, 2.5 kg, 1.0 kg, 0.9 kg, 0.8 kg, 0.7 kg, 0.6 kg, 0.5 kg, 0.4 kg, 0.3 kg, 0.2 kg or 0.1 kg of a given value or range, including increments therein. In certain embodiments, the term "about" or "approximately" means within 1 hour, within 45 minutes, within 30 minutes, within 25 minutes, within 20 minutes, within 15 minutes, within 10 minutes, within 5 minutes, within 4 minutes, within 3 minutes within 2 minutes, or within 1 minute. In certain embodiments, the term "about" or "approximately" means within 20.0 degrees, 15.0 degrees, 10.0 degrees, 9.0 degrees, 8.0 degrees, 7.0 degrees, 6.0 degrees, 5.0 degrees, 4.0 degrees, 3.0 degrees, 2.0 degrees, 1.0 degrees, 0.9 degrees, 0.8 degrees, 0.7 degrees, 0.6 degrees, 0.5 degrees, 0.4 degrees, 0.3 degrees, 0.2 degrees, 0.1 degrees, 0.09 degrees. 0.08 degrees, 0.07 degrees, 0.06 degrees, 0.05 degrees, 0.04 degrees, 0.03 degrees, 0.02 degrees or 0.01 degrees of a given value or range, including increments therein.

As used herein, and unless otherwise specified, the term "plurality," and like terms, refers to a number (of things) comprising at least one (thing), or greater than one (thing), as in "two or more" (things), "three or more" (things), "four or more" (things), etc.

As used herein, the terms "connected," "operationally connected," "coupled", "operationally coupled," "operationally linked," "operably connected," "operably coupled," "operably linked," and like terms, refer to a relationship (mechanical, linkage, coupling, etc.) between elements whereby operation of one element results in a corresponding, following, or simultaneous operation or actuation of a second element. It is noted that in using said terms to describe inventive embodiments, specific structures or mechanisms that link or couple the elements are typically described. However, unless otherwise specifically stated, when one of said terms is used, the term indicates that the actual linkage or coupling may take a variety of forms, which in certain instances will be readily apparent to a person of ordinary skill in the relevant technology.

As used herein, the terms "comprises," "comprising", or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to ½, 1, 2, or 3 is equivalent to greater than or equal to ½ of something, greater than or equal to 1, greater than or equal to 2, or greater than or equal to 3 of something.

As used herein, whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the terms "user", "end user" or "end-user" are interchangeably used. As used herein, and unless otherwise specified, these terms refer to a person or customer who ultimately uses or is intended to ultimately use a product. End users may or may not be "customers" in the usual sense; they are commonly employees of the customer. For example, if a large retail corporation buys a software package for its employees to use, even though the large retail corporation was the "customer" which purchased the software, the end users are the employees of the company, who will use the software at work. In an alternate example, hospitals which purchase power tools and medical devices for its employees (doctors and nurses) to use, even though the hospital was the "customer" which purchased the power tools and medical devices, the end users are the employees, doctors and nurses of the hospital, who will use the tools and medical devices in surgery.

As used herein, and unless otherwise specified, the term "anterior" refers to human anatomy and means the front surface of the body; often used to indicate the position of one structure relative to another, that is, situated nearer the front part of the body. Alternately, it may also refer in a similar fashion to an apparatus or structure and means the means the front surface of a device or item.

As used herein, and unless otherwise specified, the term "posterior" refers to human anatomy and means the back surface of the body; Often used to indicate the position of one structure relative to another, that is, nearer the back of the body. Alternately, it may also refer in a similar fashion to an apparatus or structure and means the back or rear surface of a device or item.

As used herein, and unless otherwise specified, the term "superior" refers to human anatomy and means situated nearer the vertex of the head in relation to a specific reference point; opposite of inferior. It may also mean situated above or directed upward. Alternately, it may also refer in a similar fashion to an apparatus or structure and means a top surface or above a top surface of a device or item.

As used herein, and unless otherwise specified, the term "inferior" refers to human anatomy and means situated nearer the soles of the feet in relation to a specific reference point; opposite of superior. It may also mean situated below or directed downward. Alternately, it may also refer in a similar fashion to an apparatus or structure and means a bottom surface or below a bottom surface of a device or item.

As used herein, and unless otherwise specified, the term "medial" refers to human anatomy and means situated toward the median plane or midline of the body. Alternately, it may also refer in a similar fashion to an apparatus or structure and means situated toward the median plane or midline of a device or item.

As used herein, and unless otherwise specified, the term "lateral" refers to human anatomy and means denoting a position farther from the median plane or midline of the body or a structure. It may also mean "pertaining to a side". Alternately, it may also refer in a similar fashion to an apparatus or structure and means denoting a position farther from the median plane or midline of a device or item.

As used herein, the term "proximity" means nearness in space or relationship, but not excluding the potential to be touching. Proximity is also alternatively meant to mean that one thing may be so close to another thing as to be "in direct or nearly direct contact" (in proximity) with another thing along some point. To "place something in proximity" is also meant to mean that items are "paired" or "mated together" either in their paired function or at some point of contact.

As used herein, and unless otherwise specified, the term "vertical", "vertically oriented" and similar terms mean; generally perpendicular to, at, or near, right angles to a horizontal plane; in a direction or having an alignment such that the top of a thing is above the bottom. In certain embodiments, the term "vertically oriented" means within ±20.0 degrees, ±15.0 degrees, ±10.0 degrees, ±9.0 degrees, ±8.0 degrees, ±7.0 degrees, ±6.0 degrees, ±5.0 degrees, ±4.0 degrees, ±3.0 degrees, ±2.0 degrees, ±1.0 degrees, ±0.9 degrees, ±0.8 degrees, ±0.7 degrees, ±0.6 degrees, ±0.5 degrees, ±0.4 degrees, ±0.3 degrees, ±0.2 degrees or ±0.1 degrees of a given value or range, including increments therein.

As used herein, and unless otherwise specified, the term "horizontally oriented" and similar terms mean; generally perpendicular to, at, or near, right angles to a vertical plane; in a direction or having an alignment such that the top of a thing is generally on, or near the same plane as the bottom, both being parallel or near parallel to the horizon. In certain embodiments, the term "horizontally oriented" means within ±20.0 degrees, ±15.0 degrees, ±10.0 degrees, ±9.0 degrees, ±8.0 degrees, ±7.0 degrees, ±6.0 degrees, ±5.0 degrees, ±4.0 degrees, ±3.0 degrees, ±2.0 degrees, ±1.0 degrees, ±0.9 degrees, ±0.8 degrees, ±0.7 degrees, ±0.6 degrees, ±0.5 degrees, ±0.4 degrees, ±0.3 degrees, ±0.2 degrees or ±0.1 degrees of a given value or range, including increments therein.

As used herein, and unless otherwise specified, the term "substantially perpendicular" and similar terms mean generally at or near 90 degrees to a given line, or surface or to the ground. In certain embodiments, the term "substantially perpendicular" means within ±20.0 degrees, ±15.0 degrees, ±10.0 degrees, ±9.0 degrees, ±8.0 degrees, ±7.0 degrees, ±6.0 degrees, ±5.0 degrees, ±4.0 degrees, ±3.0 degrees, ±2.0 degrees, ±1.0 degrees, ±0.9 degrees, ±0.8 degrees, ±0.7 degrees, ±0.6 degrees, ±0.5 degrees, ±0.4 degrees, ±0.3 degrees, ±0.2 degrees or ±0.1 degrees of a given value or range, including increments therein.

As used herein, and unless otherwise specified, the term "power tool", "medical tool", "equipment", "instrument", "devices" and similar terms refers to any type of battery-powered instrument commonly found in a hospital, surgical, or emergency medical setting. These may include, but are not limited to saws, drills, reamers, impacting tools, burring tools, cautery instruments, illuminating instruments, surgical robots and robotic tool accessories. This is not intended to be an exhaustive list, but merely an illustrative listing for the potential applications of this device and methods.

Further still, said battery powered medical device may further comprises a sterile surgical equipment such as surgical staplers, robot assisted equipment, robotics, endoscopic and laparoscopic equipment, electrosurgery equipment, powered screwdrivers and potentially, any field hospital equipment such as suction tools, devices and systems and respiratory assist devices operated under battery or a battery back-up power device.

As used herein, and unless otherwise specified, the term "device", and similar terms refers to any device or tool requiring a battery, preferably for a hospital, surgical, or emergency medical setting. Device may also refer to a power tool, such as a battery-operated power tool. In a preferred embodiment, a device refers to medical device of any kind requiring a battery. In a more preferred embodiment, a device refers to a "sterile" medical device intended for a sterile medical procedure. In still a further preferred embodiment, a device refers to a "sterile" medical power tool intended for a sterile medical procedure such as a surgical procedure. In yet another preferred embodiment, a device refers to a "non-sterile" medical power tool intended for a sterile medical procedure such as a surgical procedure, following a suitable sterility protocol being done to prepare it for a sterile procedure.

As used herein, and unless otherwise specified, the term "reusable" and similar terms mean or refer to a device that was designed and intended for long term, repeated use over an extended period of time.

As used herein, the phrase "limited-use" and similar terms mean or refer to a device that was designed and intended for short term, repeated use over a limited period of time. Limited-use items may also be recyclable or capable of being refurbished by the manufacturer to bring it back up to "new" status or at least some minimum acceptable standard.

As used herein, and unless otherwise specified, the phrase "limited-use" as applied to orthopedic surgical tools can mean having a limited useful life, or a restricted lifespan for intended use. Preferably in this context, limited-use is intended to mean the number of surgeries where the useful life of the tool ranges from more than one use to less than 50 surgeries, and in some embodiments, where the useful life of the tool ranges from more than one use to less than 30 surgeries, and in still further embodiments, where the useful life of the tool ranges from more than one use to less than 20 surgeries.

As used herein, and unless otherwise specified, the phrase "reusable" as applied to "limited-use" orthopedic surgical tools described herein can mean a surgical tool that is configured for limited-use, but is intended for re-use a limited number of times before refurbishment of one or more components is required, other than routine re-sterilization. Reuseable tools, as defined herein, may be provided to an end-user on multiple occasions, within limits as defined above, as an individual pre-sterilized surgical tool or a pre-sterilized surgical tool system with multiple separated components, such as, by way of example: a drill with disposable or single-use drill bits and either an included or separated battery; or a saw with disposable or single-use saw blades and either an included or separated battery; all provided in a pre-sterilized disposable packaging system. Such tools would then routinely be returned to the manufacturer, after every use, for cleaning, refurbishment as needed, repackaging and re-sterilization.

As used herein, and unless otherwise specified, the terms "disposable," "single-use" and similar terms mean or refer to a device that was designed and intended for one application only. When labeled as "disposable," the product is intended to be, and likely should be discarded after its initial use. As used herein, "single-use" may also refer to a device that is recyclable or capable of being refurbished by the manufacturer to bring it back up to "new" status or at least some minimum acceptable standard.

As used herein, and unless otherwise specified, the term "elastomer", "elastomeric" and similar terms mean or refer to materials that are polymeric materials which have the property of elasticity or viscoelasticity. An elastomeric material can be any material exhibiting elastic or rubber-like properties, the ability to deform and return to its original shape. Generally speaking, elastomeric materials are measured in material type, compound, and durometer. By virtue of this elasticity in combination with their damping capability, (power/length*temperature i.e.: W/m*K or Loss Factor), elastomers are the preferred material for use as transmission elements in elastic or highly elastic couplings. In general terms, elastomers are often simply referred to as rubber. Examples of elastomeric materials include but are not limited to: rubbers such as acrylonitrile butadiene rubber, styrene butadiene rubber and Buna-N rubber (Nitrile); and other polymers such as polychloroprene (neoprene), ethylene vinal acetate (EVA), polyvinyl chloride (PVC), ethylene propylene, fluoroelastomer, silicone, closed cell silicone sponge, fluorosilicone and polyisobutylene. In one or more preferred embodiments as described herein, elastomeric materials of choice include: extruded vinyl materials that meet UL 94 V0 flammability requirements; (commonly used in hospital equipment, electronics, and computer housings); or EVA Polymers or PVC/EVA copolymers which are well known for both vibration damping and noise reduction. Others may include hybrid materials or specialized engineering polymers and proprietary compounds.

As used herein, and unless otherwise specified, the term “integrated” and similar terms mean or refer to something that is incorporated into or with something else to make a complete unit. As used herein, a device may have another separable sub-component “integrated” or “assembled” into the device itself creating a fully assembled device within the packaging when it is received by an end user. Or alternately, a device may have a separable sub-component integrated into the packaging of the device, but not assembled to the device itself within the packaging. As such, the sub-component can be assembled by an end user once the combined unit packaging is opened.

Alternately the term “non-integrated” as used herein, means or refers to something that is not incorporated into a complete assembly or assembled to make a complete unit. As used herein, a device may have another separable sub-component that is “non-integrated” or “not assembled” into the device itself creating a partially assembled device within the packaging when it is received by an end user. As such, a device may have a separable sub-component that is not in the packaging of the device and is packaged separately in its own packaging. As such, the sub-component can be assembled by an end user to the device once the two components are brought together. For example, a power saw may have the ability to fitted with multiple types of saw blade chucks, each having a unique or special purpose capable of holding multiple types of saw blades. The same scenario would apply to drills and drill chucks. Further still, a similar scenario would apply to any battery powered device capable of receiving batteries having different power capabilities, sizes, sterile versus non-sterile, etc.

As used herein, and unless otherwise specified, the term “offset shaft” and similar terms mean or refer to a drive shaft or power delivery shaft used to transfer power from a motor (driver) to a piece of equipment (driven) or another drive shaft or power delivery shaft. Offset denotes that the shafts of the driver and driven elements are not “inline” with each other. In some embodiments, an offset shaft may utilize u-joints (a “cardan shaft”) to generate the offset.

As used herein, and unless otherwise specified, the term “control processor”, CPU" and similar terms mean or refer to back-end devices that make a control system operate. The control processor in a Central Controller receives user interactions from User Interface devices, (i.e.: triggers, etc.), and then tells the controlled devices (i.e.: drills, saws, medical instrument(s) or TV, digital player/recorder, lights, screens, etc.) to perform the desired action.

As used herein, and unless otherwise specified, combinations such as “at least one of A, B, or C.” “one or more of A, B, or C.” “at least one of A, B, and C,” “one or more of A, B, and C.” and “A, B, C, or any combination thereof” include any combination of A, B, and/or C, and may include multiples of A, multiples of B, or multiples of C. Specifically, combinations such as “at least one of A, B, or C.” “one or more of A, B, or C.” “at least one of A. B, and C.” “one or more of A, B, and C.” and “A, B, C, or any combination thereof” may be A only, B only, C only, A and B, A and C, B and C, or A and B and C, where any such combinations may contain one or more member or members of A, B, or C.

Provided herein is a modular system comprising a limited-use, battery-operated orthopedic hand tool having modular internal components; said modular internal components comprising: a variable speed motor providing a rotational output; an internal drive mechanism comprising; a first drive shaft; a motor shaft coupling; an offset shaft; and at least one drive shaft bearing; one or more elastomeric dampers; an external housing comprising a handle grip; a trigger mechanism to control the variable speed motor; a trigger control processor, a rechargeable battery; and a battery compartment.

As illustrated in FIGS. 1, 2A, 2B and 3, a first embodiment of a surgical saw with internal damping features is shown. FIG. 1 illustrates an exterior front view of a surgical saw 100 comprising a housing base 101*a*, a housing handle 101*b*, a drive motor housing 102*b*, a drive trigger 114, a drive trigger, a trigger lock tab 103, a quick connect saw blade module 115 and module housing 115*b* and a (saw) blade lock lever 121.

Figure 2A:
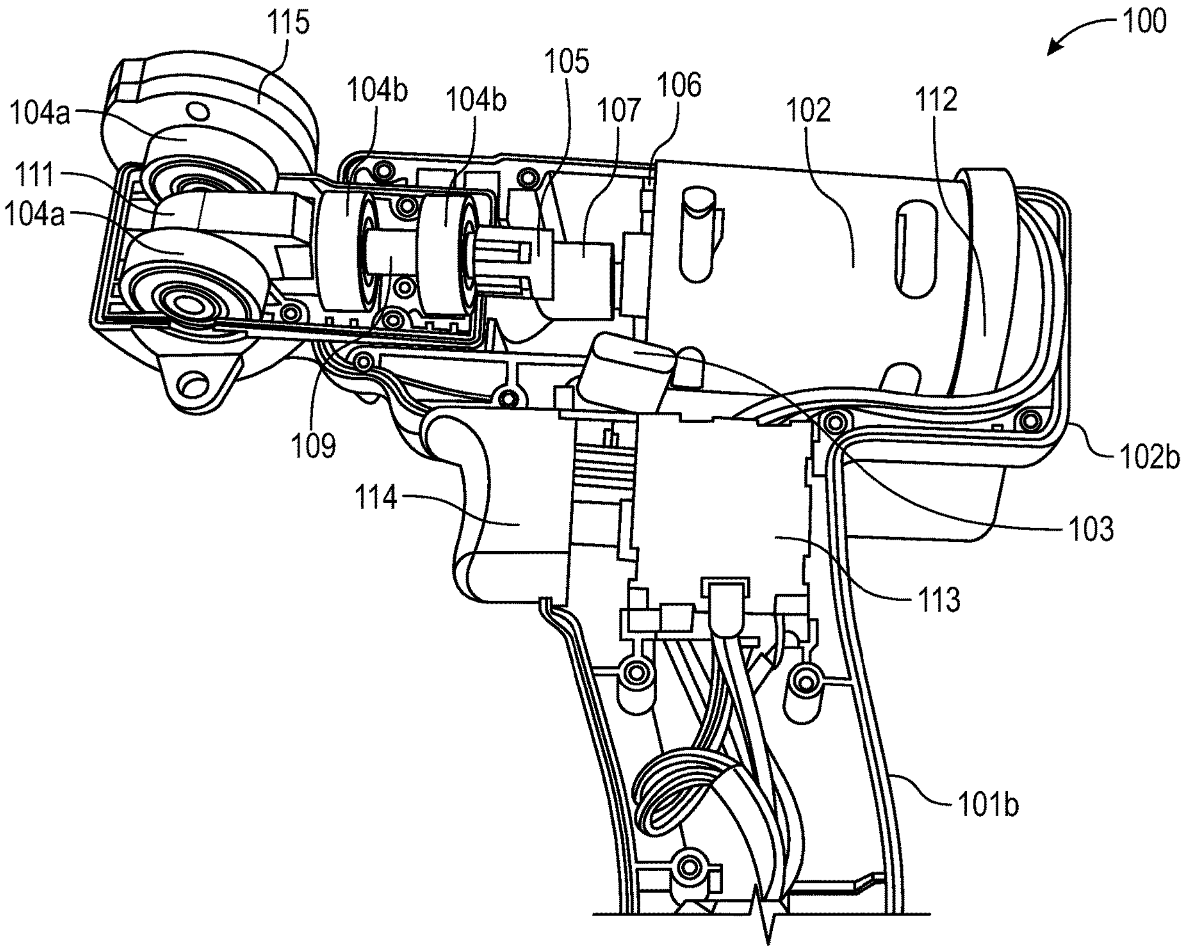
FIG. 2A is a cut-away orthogonal side section view of FIG. 1, illustrating a possible configuration of the modular internal drive components with an offset shaft drive coupling, an offset shaft, a short fork shaft and gear drive shaft, trigger and trigger control processor.
Figure 2B:
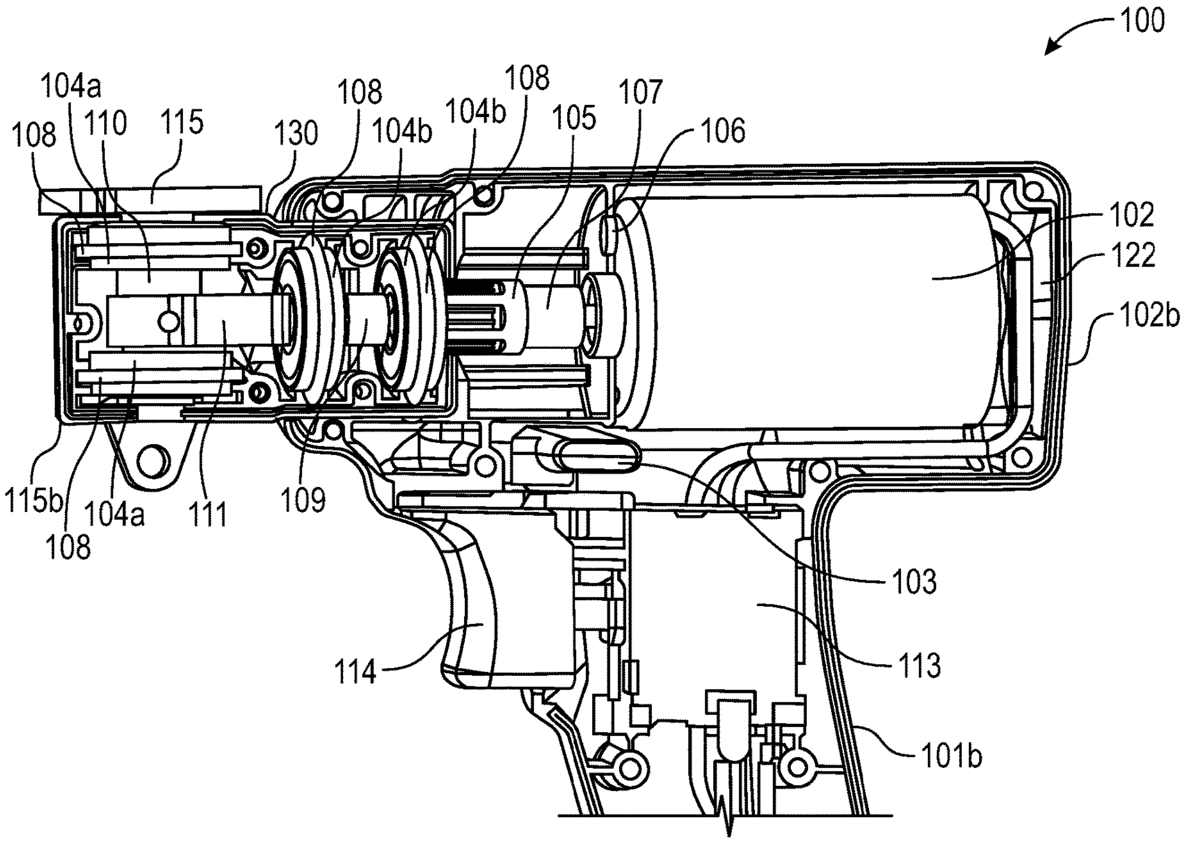
FIG. 2B is a graphical side section view of FIG. 2A.

As further shown in FIGS. 2A and 2B are detailed orthographic section side views illustrating the first embodiment of the surgical saw 100 comprising the housing handle 101*b*, a drive motor housing sub-assembly 102*b*, comprising an electro-mechanical drive motor 102, and motor mount 106, the drive trigger 114, a trigger controller processor 113, the trigger lock tab 103, a plurality of shaft bearings 104*a*, an offset shaft drive coupling 105, a fork drive gear connector 107, a singular or plurality of damping elements 108 around the shaft bearings and strategically placed between the housing and drive mechanism components, an offset shaft 109 and a pivot link-offset driver 111, the quick connect saw blade module 115 and module housing 115*b* comprising a pivot shaft 110, a singular or plurality of pivot shaft bearings 104*b*, additional damping elements 108 and with internal damping features strategically placed between the internal housing and various mounting structures within the housing and wherein the system further comprises: at least one elastomeric damper 108 fitted about a support of the offset shaft; wherein the damper could be placed; around a support bearing or bearings; about the sides of the support bearing or bearings; around the support bearing and either or both ends of the variable speed motor; or anywhere around the exterior of the support bearings and variable speed motor and within the external housing.

In some embodiments of the first embodiment 100, within the quick-connect saw blade module 115, there is an offset shaft 109 with a fork on the end (pivot link—offset driver 111) extending perpendicular to the axis of the pivot shaft 110, and a cutting blade (not shown) which extend from a secondary shaft (not shown). This pivot shaft 110 is supported by bearings 104*a* which are disposed in a housing 115*b*. The fork extends and interfaces with a bearing 104*b* on the offset shaft 109 with an axis perpendicular to the pivot shaft 110 on which the bearing 104*b* is offset from the axis of the offset shaft 109 to create side to side movement of the fork when rotating, which causes the pivot shaft to oscillate. This shaft is supported by a bearing or bearings disposed in a housing. Sources of vibration and noise come from the interface between the fork and the offset bearing, and the cutting blade and connection to the oscillating shaft. To damp this vibration and decrease the propagation of the vibration, elastomeric material is placed between the bearings and the housing of the bearings and/or elastomer(s) can be place between the module which houses these bearings and shafts and a main housing (handle) of the device. The elastomeric dampers can be in the form of an O-ring shape, strips, blocks, threaded mounts or co-molded elements.

In some embodiments, the system further comprises: an elastomeric damper 112 fitted about the variable speed motor 102; wherein the damper could be placed about; a posterior end thereof; an anterior end thereof; both the anterior and posterior end thereof, or anywhere around the exterior of the variable speed motor.

In some embodiments of the system, the drive mechanism comprises one or more elastomeric dampers 108, 112 having a durometer between Shore A 60-100 or between Shore D 0-60 about or around the first drive shaft, the first output shaft, the second drive shaft, the second output shaft, all of the bearings and the drive motor.

In some embodiments, the system further comprises a drive mechanism shroud, also known as a casing, 130, surrounding the internal drive mechanism comprising the plurality of shaft bearings 104*a*, the offset shaft drive coupling 105, the fork drive gear connector 107, the plurality of damping elements 108 around the shaft bearings and strategically placed between the housing and drive mechanism components, the offset shaft 109 and the pivot link-offset driver 111.

In some embodiments of the system, the drive mechanism shroud, also called a casing 130, internally comprises one or more elastomeric dampers having a durometer between Shore A 60-100 or between Shore D 0-60.

In some embodiments of the system, the drive mechanism shroud 130 externally comprises one or more elastomeric dampers having a durometer between Shore A 60-100 or between Shore D 0-60.

In some embodiments, the system further comprises one or more elastomeric dampers 108 having a durometer between Shore A 40-100 in the battery compartment.

In some embodiments, the system further comprises: a second drive shaft, also known as a pivot shaft 110 for the quick connect saw blade module 115, configured at a different orientation (e.g.: 90°) to the offset shaft 109; at least one bearing on the second drive shaft 110; and an attachment receiver 115*b* coupled to the second drive shaft for modular attachments (i.e.: saw blades) used for performing surgical procedures; wherein the second drive shaft 110 and the at least one bearing 104*a* on the second drive shaft further comprise elastomeric damping features 108.

In some embodiments of the system, the variable speed motor 102 is configurable to drive the second drive shaft 110 in a range between 8,500-10,500 oscillations per minute (OPM).

In some embodiments of the system, the elastomeric dampers 108 maintain a sound level of 80-90 dB or less when the system is running.

In some embodiments of the system, the elastomeric dampers 108 decrease the amplitude of vibration from undamped systems by 10%-30% when the system is running with a cutting blade installed.

In some embodiments, the system further comprises a counterbalance weight 122 within the external housing, to balance the weight of the modular system in a user's hand.

Figure 3:
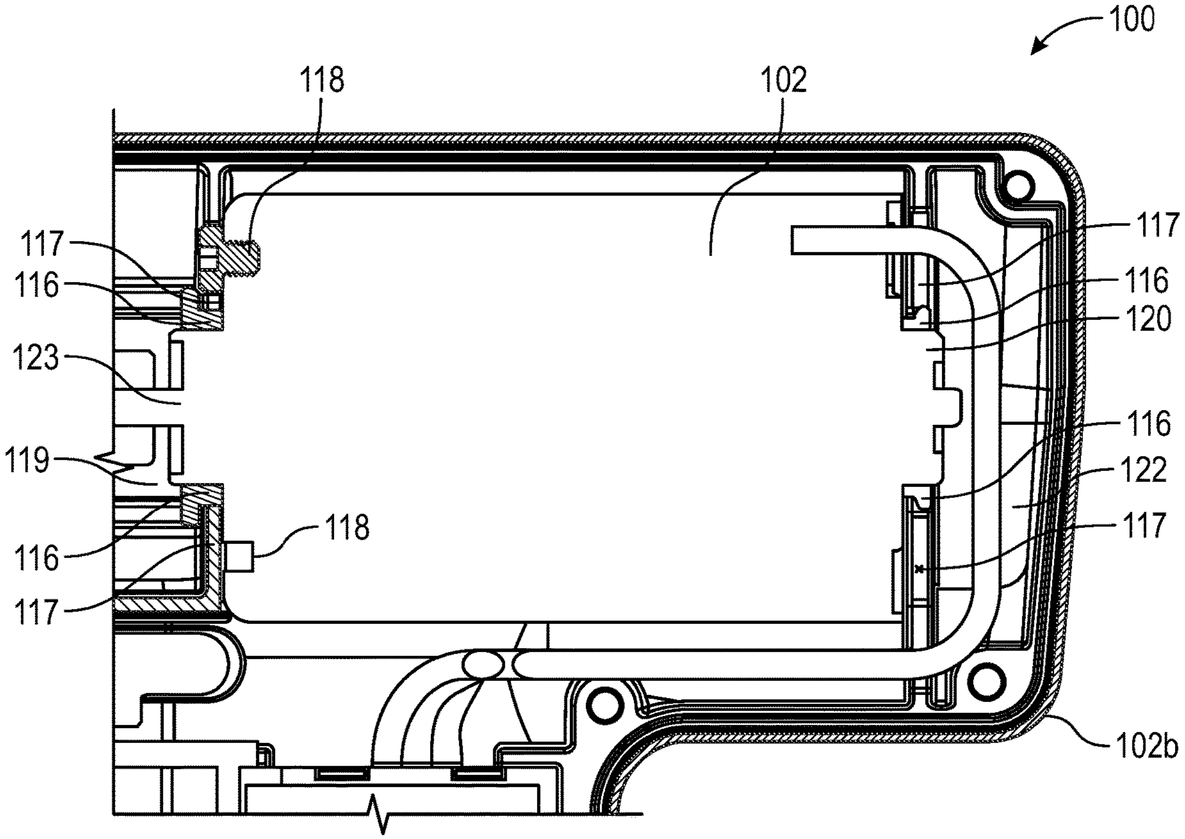
FIG. 3 is a partial section view of the electro-mechanical drive motor housing of FIG. 2B.

As further shown in FIG. 3, is a detailed side view of the drive motor and external housing of the first embodiment of the surgical saw with internal damping features. FIG. 3 illustrates a section view of surgical saw 100 comprising a drive motor housing 102*b*, an electro-mechanical drive motor 102, a drive motor output shaft 123, a plurality of elastomer motor mount supports 116, a plurality of housing motor mounts 117 and motor mount screws 118, a front motor housing mount 119 and a rear motor housing mount 120. In addition, the entire electro-mechanical drive motor 102 may also be at least partially surrounded or encased in one or more elastomeric damping elements. In alternate embodiments, the electro-mechanical drive motor 102 may have elastomeric damping elements fitted about an anterior portion, a posterior portion, or both the anterior and posterior portions or ends, within the drive motor housing 102*b*. In still further alternate embodiments, the electro-mechanical drive motor 102 may have an elastomeric damping element fitted about at least about ½ of the dive motor, within the drive motor housing 102*b*.

Figure 4:
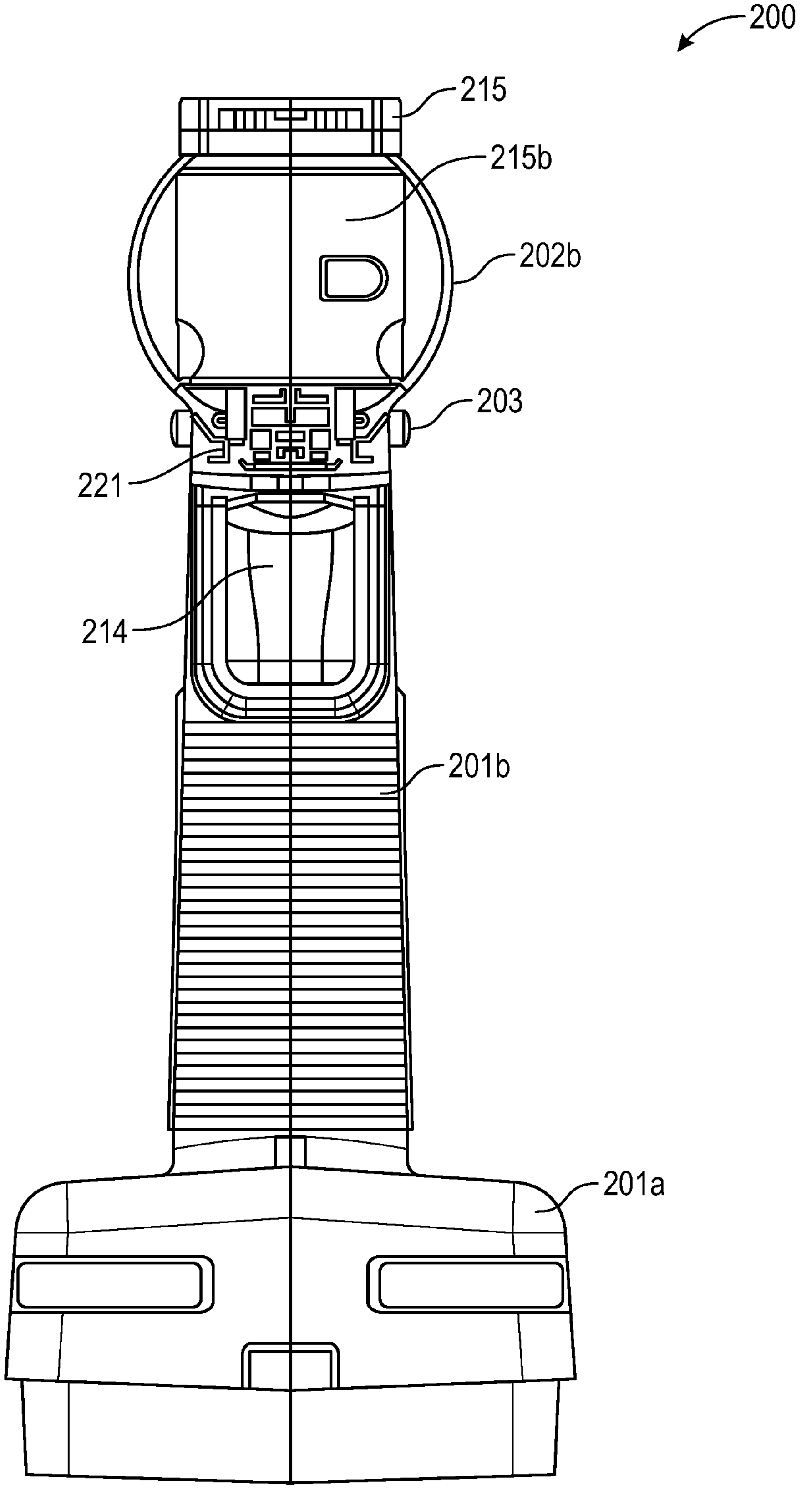
FIG. 4 is a front view of a battery-operated orthopedic hand tool saw having modular internal components with an electro-mechanical drive motor, an offset shaft and an extended pivot link.

In another embodiment, FIGS. 4, 5, 6A, 6B and 7, a second embodiment of a surgical saw with internal damping features is shown. FIG. 4 illustrates a typical exterior front view of a surgical saw 200 comprising a housing base 201*a*, a housing handle 201*b*, a drive motor housing 202*b*, a drive trigger 214, a drive trigger, a speed lock tab 203, a quick connect saw blade module 215 and module housing 215*b* and a (saw) blade lock lever 221.

Figure 5:
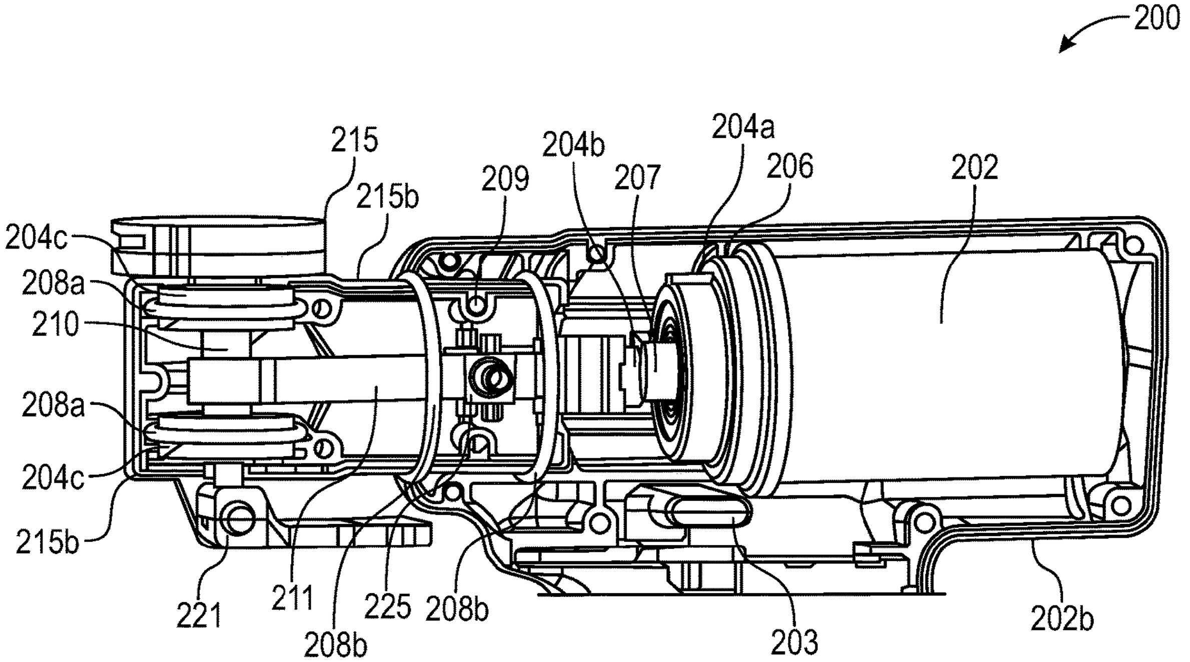
FIG. 5 is an illustrative representation of a cut-away side section view of the proximal body of FIG. 4, illustrating a possible configuration of the modular internal drive components with an electro-mechanical drive motor, an offset shaft and an extended pivot link connecting to an anterior saw blade module.

FIG. 5 is an illustrative representation of a cut-away side section view of the proximal body 202*b* of the surgical saw 200 shown in FIG. 4, illustrating a possible configuration of the modular internal drive components with an electro-mechanical drive motor 202, an offset shaft 207 and an extended pivot link 211 connecting to an anterior quick-connect saw blade module 215. Also shown in this view are external components including the trigger lock tab/speed lock tab 203, and the blade lock lever 221 for securing a saw blade within the quick-connect saw blade module 215.

Further, FIG. 5 illustrates alternative embodiments of the drive mechanism including a radial support bearing 204*a* nested inside an elastomeric bearing and motor mount 206, which supports a drive motor output shaft (not shown in this view) emanating from the electro-mechanical drive motor 202. The drive motor output shaft couples to an offset shaft 207, which is supported by at least one offset bearing 204*b*. The offset shaft 207 in turn couples to an extended, or long, pivot link 211, which in turn is supported by one or more pivot link brackets 225. The pivot link bracket 225 is supported and mounted to the internal sides of the of the proximal saw housing 202*b* in one or more locations above and below the long pivot link 211 and held in place with mounting set screws and further secured with elastomeric damper materials 209 in and around the pivot link bracket mounts with module mount damping elements 208*b* to provide additional vibration damping. Further still, the extended, or long, pivot link 211, may further be at least partially secured within a distal portion of a shroud or quick connect saw blade module housing 215*b*, which in turn is a part of the quick-connect saw blade module 215.

Further still, as shown in FIG. 5, a modified variant of the surgical saw 200 illustrating internal components of the quick-connect saw blade module 215 are shown. Herein, the pivot shaft 210 for the quick-connect saw blade module is supported by at least two pivot shaft bearings 204*c* which in turn are supported and surrounded by vibration damping elements 208*a*.

Figure 6A:
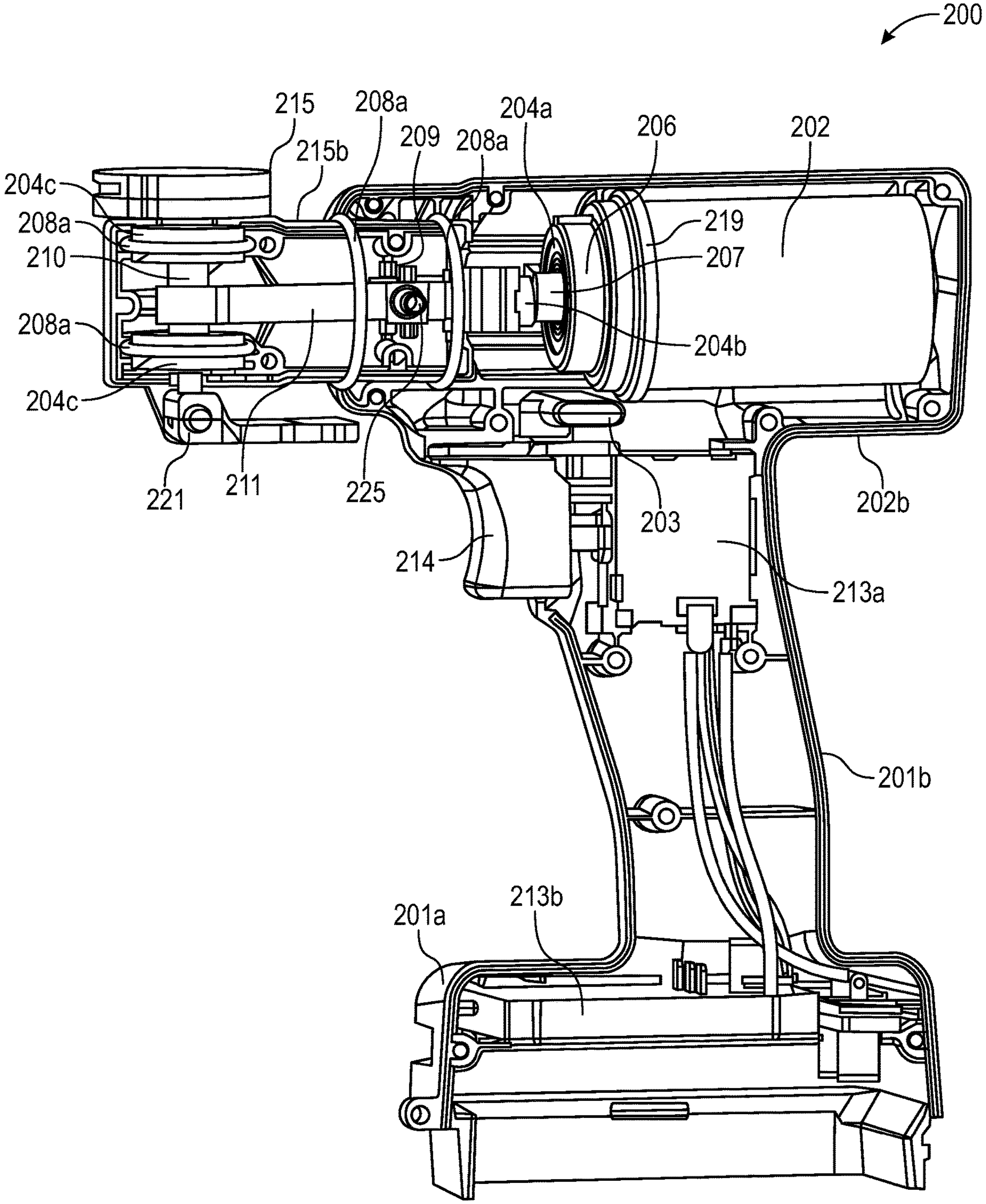
FIG. 6A is a further illustrative representation of an orthogonal cut-away side section view of the entire saw body of FIG. 5, illustrating a possible configuration of the modular internal drive components with an electro-mechanical drive motor, an offset shaft and an extended pivot link connecting to an anterior saw blade module, a speed control trigger, a trigger controller-processor, a motor controller and partial section view of a battery compartment.
Figure 6B:
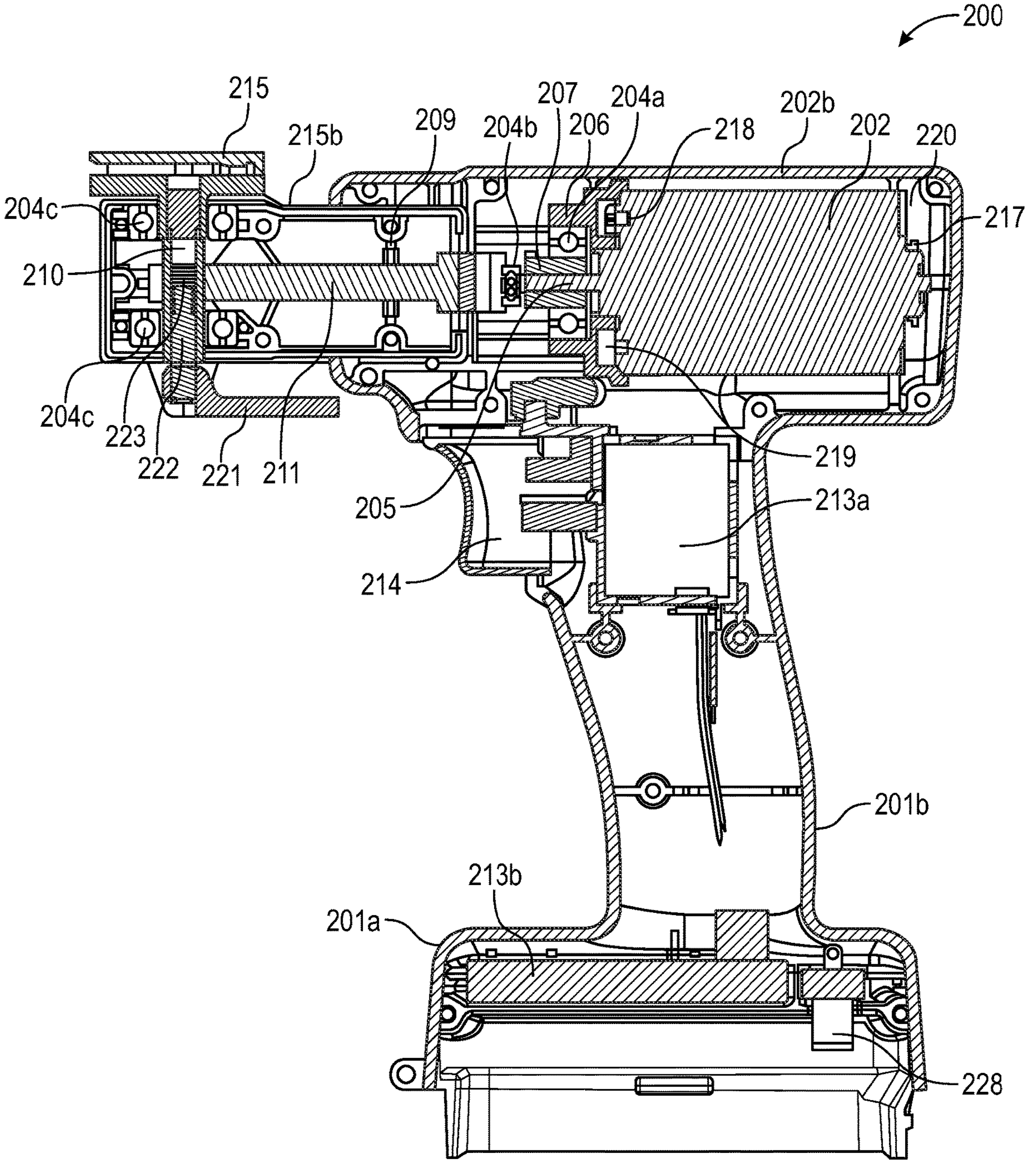
FIG. 6B is a further illustrative representation of a cut-away side section view of the proximal body of FIG. 6A, illustrating a possible configuration of the modular internal drive components with an electro-mechanical drive motor, an offset shaft and an extended pivot link connecting to an anterior saw blade module, a speed control trigger, a trigger controller-processor, a motor controller and partial section view of a battery compartment.

Moving on to FIGS. 6A & 6B; FIG. 6A is a further illustrative representation of an orthogonal cut-away side section view of the entire saw body of FIG. 5, further illustrating the extended pivot link configuration of the modular internal drive components of the saw with an electro-mechanical drive motor 202, an offset shaft 207 and an extended pivot link 211 connecting to an anterior saw blade module 215, a trigger lock tab/speed lock tab 203, a speed control trigger 214, a trigger controller-processor 213*a*, a motor controller 213*b*, residing in the base/handle housing 201*b* and a partial section view of a battery compartment 201*a*. FIG. 6A also provides graphical illustrative representations of embodiments of the drive mechanism including a radial support bearing 204*a* nested inside an elastomeric bearing and motor mount 206, which supports a drive motor output shaft (not shown in this view) emanating from the electro-mechanical drive motor 202. The drive motor output shaft couples to an offset shaft 207, which is supported by at least one offset bearing 204*b*. The offset shaft 207 in turn couples to an extended, or long, pivot link 211, which in turn is supported by one or more pivot link brackets 225. The pivot link bracket 225 is supported and mounted to the internal sides of the of the proximal saw housing 202*b* in one or more locations above and below the long pivot link 211 and held in place with mounting set screws and further secured with elastomeric damper materials 209 in and around the pivot link bracket mounts with module mount damping elements 208*b* to provide additional vibration damping. Further still, the extended, or long, pivot link 211, may further be at least partially secured within a distal portion of a shroud or quick connect saw blade module housing 215*b*, which in turn is a part of the quick-connect saw blade module 215.

FIG. 6B is a further illustrative representation of a cut-away side section view of the proximal body of FIG. 6A, illustrating a possible configuration of the modular internal drive components with an electro-mechanical drive motor 202, the motor output shaft 205, surrounded by a radial support bearing 204*a* nested inside an elastomeric bearing and motor mount 206, which supports a drive motor output shaft, an offset shaft 207 and an extended pivot link 211 connecting to an anterior saw blade module 215, a speed control trigger 214, a trigger controller-processor 213*a*, a motor controller 213*b* and partial section view of a battery compartment 201*a*, also illustrating a battery contact 228, in addition to all the other drive mechanism features illustrated in FIG. 6A. In addition, FIG. 6B, also illustrates critical elastomeric mounting dampers that have been added around the posterior diameter portion of the electro-mechanical drive motor 202, within the drive motor housing 202*b*, the elastomeric housing motor mounts 217, at the posterior end of the electro-mechanical drive motor 202, and the anterior motor mount screws 218, which may also comprise elastomeric damper material in those spaces. Also shown in this view are components including the blade lock lever 221, the blade lock dowel pin 222 and associated blade lock compression spring 223 for securing a saw blade within the quick-connect saw blade module 215.

Figure 7:
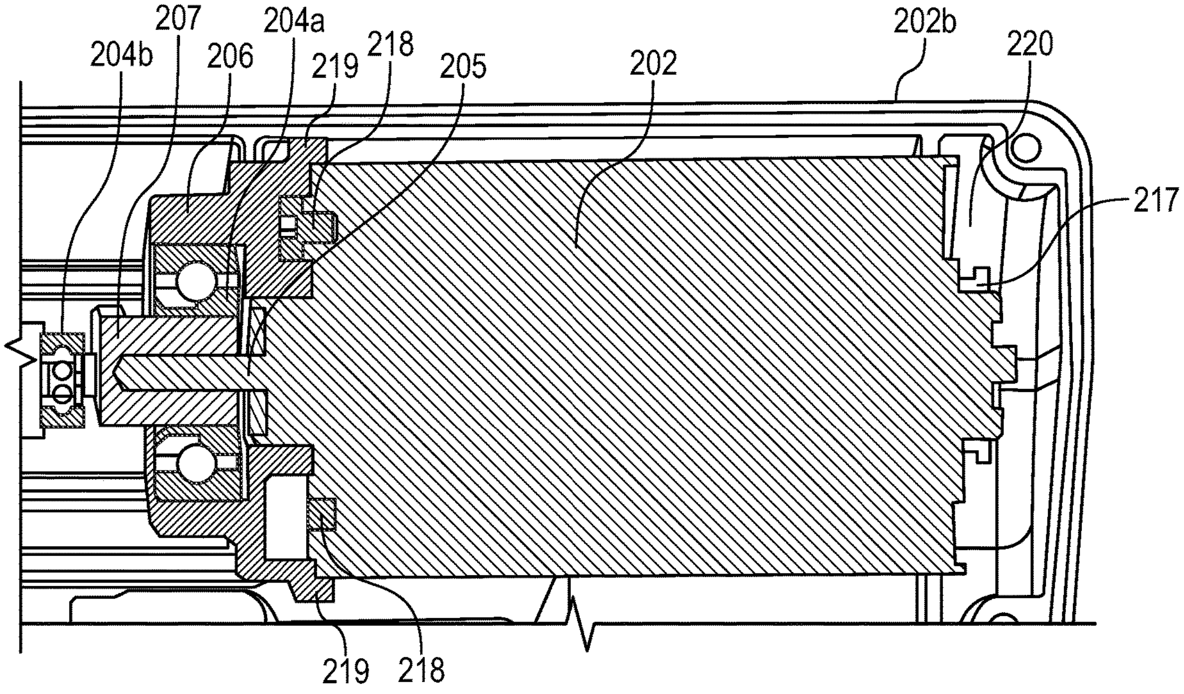
FIG. 7 is a partial section view of the electro-mechanical drive motor housing of FIG. 6B.

Moving on to FIG. 7, is an illustration of the partial section view of the electro-mechanical drive motor housing of FIG. 6B. Shown herein is a detailed side view of the drive motor and external housing of the second embodiment of the surgical saw with internal damping features. FIG. 3 illustrates a section view of surgical saw 200 comprising a drive motor housing 202*b*, an electro-mechanical drive motor 202, a drive motor output shaft 205, at least one radial support bearing 204*a*, optionally mounted within an elastomeric motor and bearing mount 206, the output shaft 205 operationally connected to an offset shaft 207, which is supported by at least one offset shaft bearing 204*b*, a plurality of posterior elastomer motor mount supports 217, an anterior elastomeric housing motor mount 219 and motor mount screws 218, and a rear motor housing mount 220. In addition, the entire electro-mechanical drive motor 202 may also be at least partially surrounded or encased in one or more elastomeric damping elements such as 219, 220. In alternate embodiments, the electro-mechanical drive motor 102 may have elastomeric damping elements fitted about an anterior portion, a posterior portion, or both the anterior and posterior portions or ends, within the drive motor housing 102*b*. In still further alternate embodiments, the electro-mechanical drive motor 102 may have an elastomeric damping element 219, 220, fitted about at least about ½ of the dive motor, within the drive motor housing 102*b*.

The second embodiment illustrated in FIGS. 4, 5, 6A, 6B and 7, may further be described as having an oscillating shaft 207 with an extending fork (long pivot link) 211 housed in one enclosure, and the offset bearing 204*b* housed in a separate enclosure, with the two enclosures mating. The oscillating shaft 207 may have damping elements 204*b* between the support bearing 204*a*, 206 and housing 202*b*. The oscillating shaft housing may have damping elements 208*b*, 209 between itself and the main device housing 202*b*, 215*b* which includes the device handle 201*b*. The motor 202 and offset bearing(s) 204*a* are disposed in the main housing, with a damping element 208*b* between the support bearing of the offset shaft 207, and the housing 202*b*, to decrease the transmission of vibration to the handle 201*a* from the interaction of the offset bearing 204*b*, and the interfacing end of the fork 211.

Figure 8:
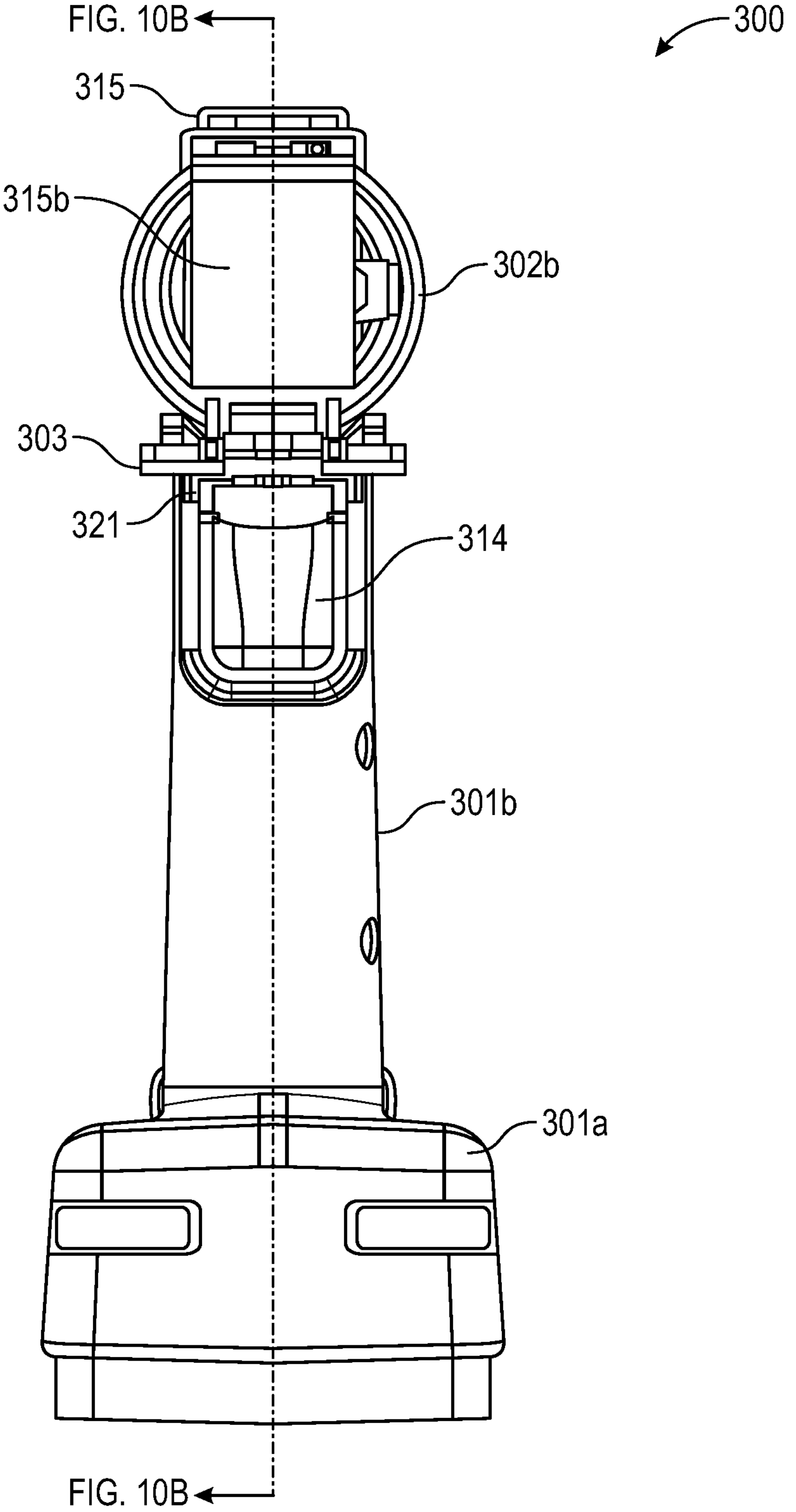
FIG. 8 is a front view of a battery-operated orthopedic hand tool saw having internal components with an electro-mechanical drive motor, an offset shaft and an extended pivot link, all of which can optionally be encased together in one vibration damping shroud or individually encased in separate, attachable shrouds for each of the electro-mechanical drive motor, the offset shaft and an extended pivot link.

Finally, FIGS. 8, 9A, 9B, 10A, 10B and 10C, illustrate a third potential embodiment 300 of the surgical saw with vibration damping with internal damping shrouds or housings to further isolate vibration from the drive mechanisms. FIG. 8 illustrates a typical exterior front view of a surgical saw 300 comprising a housing (battery) base 301*a*, a housing handle 301*b*, a drive motor housing 302*b*, a drive trigger 314, a drive trigger, a speed lock tab 303, a quick connect saw blade module 315 and module housing 315*b* and a (saw) blade lock lever 321.

Figure 9A:
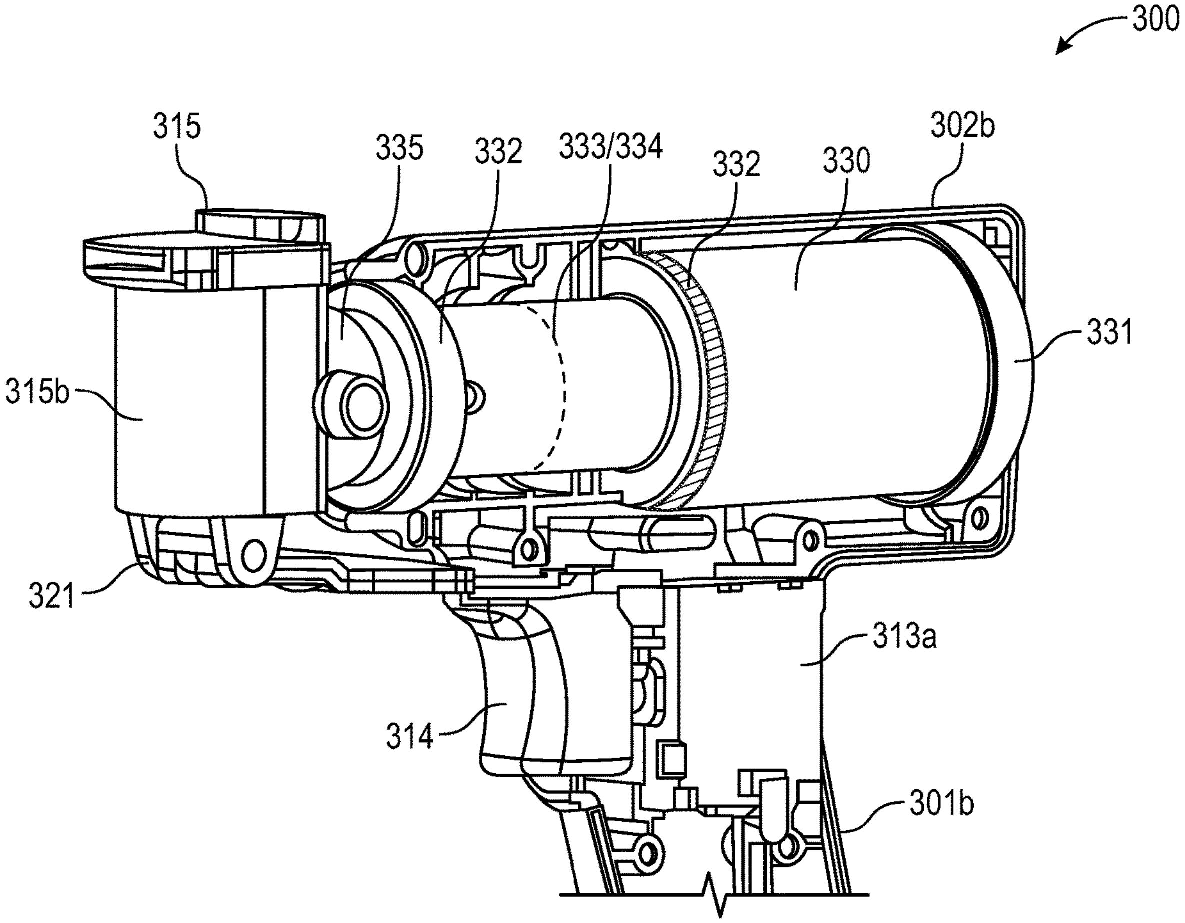
FIG. 9A is an illustrative representation of an orthogonal cut-away side section view of the entire proximal saw body and partial handle of FIG. 8, illustrating a possible configuration of the modular internal drive components with an electro-mechanical drive motor, an offset shaft and an extended pivot link, all of which illustrated as encased together in one vibration damping shroud connecting to an anterior saw blade module; a speed control trigger and a trigger controller-processor.

FIG. 9A is an illustrative representation of an orthogonal cut-away side section view of the entire proximal saw body and partial handle of FIG. 8, illustrating a possible configuration of the modular internal drive components with an electro-mechanical drive motor 302 (not shown) inside of a rigid shroud 330, posterior elastomeric damping element 331 and multiple anterior elastomeric damping elements 332 an offset shaft and an extended pivot link and support bearings, (not shown), all of which illustrated as encased together in one or more vibration damping shroud(s) 333/334 connecting to an anterior saw blade module 315, via a quick-connect housing connecting sleeve casing 335, the anterior saw blade module 315, encased in an anterior saw blade module housing 315*b*; a speed control trigger 314 and a trigger controller-processor 313*a*, configured within the base handle housing 301*b*.

Figure 9B:
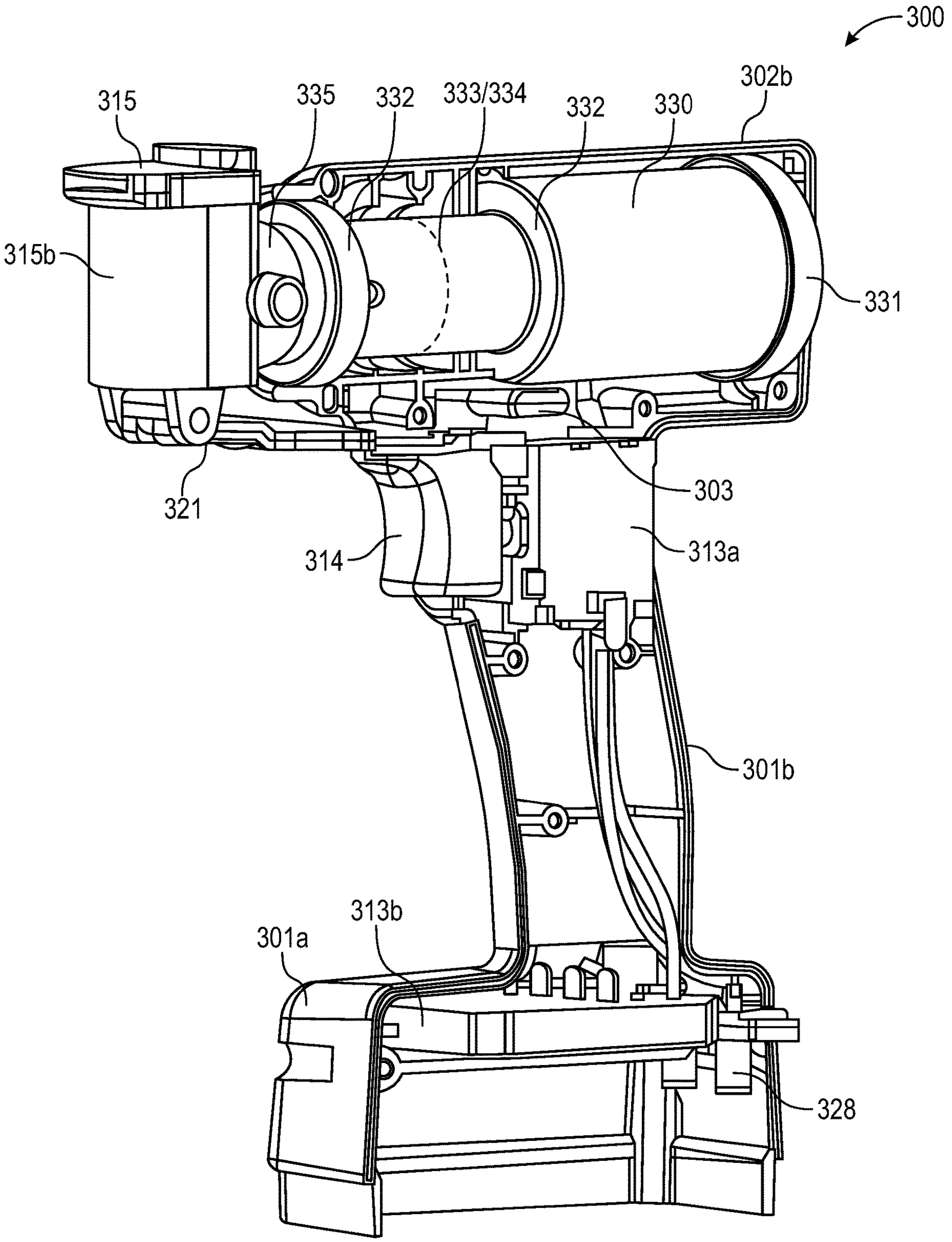
FIG. 9B is a further illustrative graphical representation of an orthogonal cut-away side section view of the entire saw body of FIG. 8, illustrating a possible configuration of the modular internal drive components with an electro-mechanical drive motor, an offset shaft and an extended pivot link, all of which illustrated as encased together in one vibration damping shroud connecting to an anterior saw blade module; a speed control trigger and a trigger controller-processor and further illustrating a motor controller and partial section view of a battery compartment.

FIG. 9B is a further illustrative graphical representation of an orthogonal cut-away side section view of the entire saw body of FIG. 9A, illustrating a possible configuration of the modular internal drive components with an electro-mechanical drive motor 302 (not shown) inside of a rigid shroud 330, posterior elastomeric damping element 331 and multiple anterior elastomeric damping elements 332, an offset shaft and an extended pivot link and support bearings, (not shown), all of which illustrated as encased together in one or more vibration damping shroud(s) 333/334 connecting to an anterior saw blade module 315, via a quick-connect housing connecting sleeve casing 335, the anterior saw blade module 315, encased in an anterior saw blade module housing 315*b*; a speed control trigger 314 and a trigger controller-processor 313*a*, configured within the base handle housing 301*b*. Also shown are the base battery housing 301*a*, the electromechanical motor controller 313*b* and the battery contact(s), both configured within the base battery housing 301*a*.

Figure 10A:
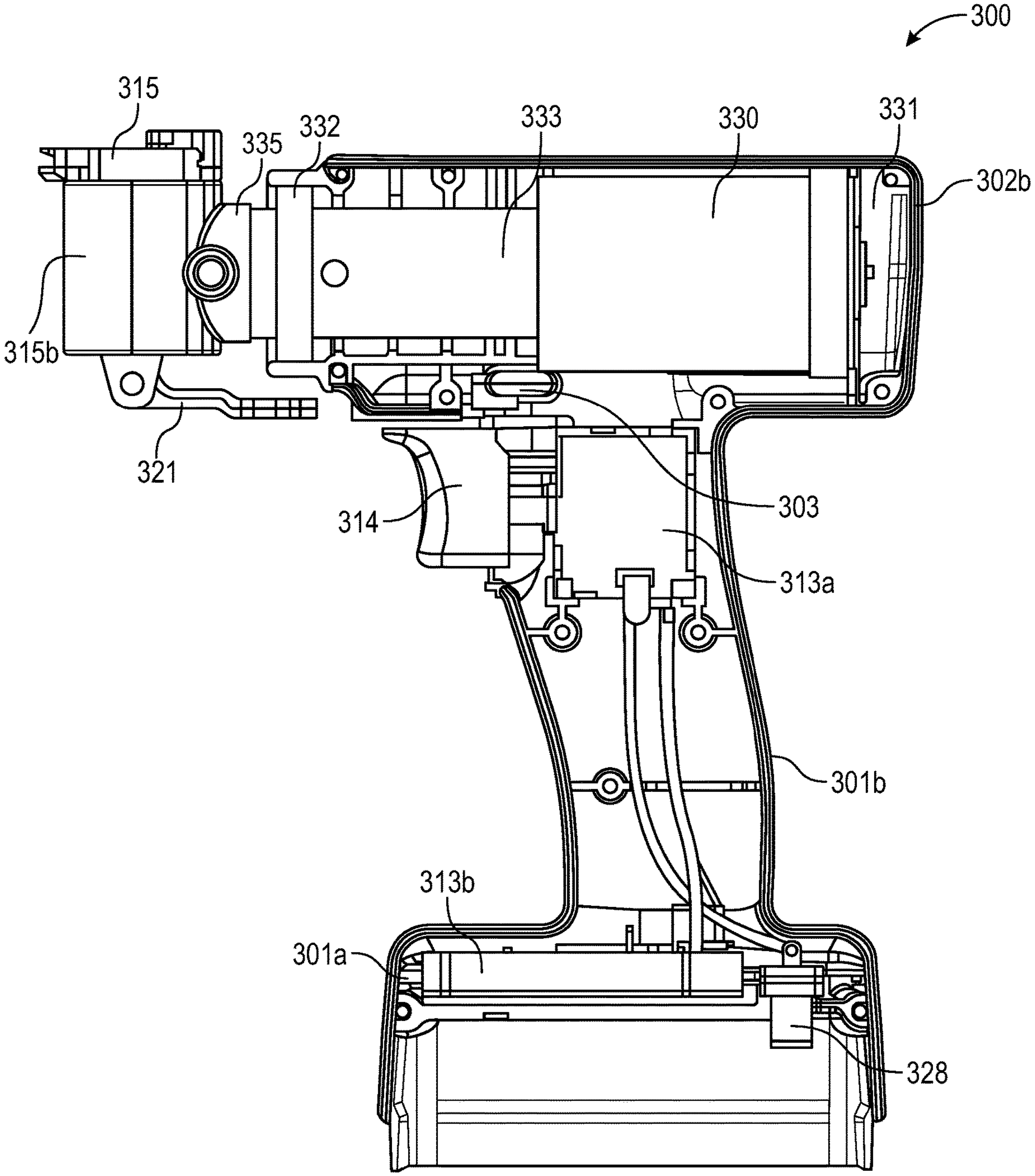
FIG. 10A is a further illustrative graphical representation of an orthogonal cut-away side section view of the entire saw body of FIG. 8, illustrating another possible configuration of the modular internal drive components with an electro-mechanical drive motor, an offset shaft and an extended pivot link, all of which illustrated as encased in multiple adjoining vibration damping shrouds connecting to an anterior saw blade module; a speed control trigger and a trigger controller-processor and further illustrating a motor controller and partial section view of a battery compartment.

FIG. 10A is a further illustrative graphical representation of a cut-away side section view of the entire saw body of FIG. 9B, illustrating another possible configuration of the modular internal drive components with an electro-mechanical drive motor 302 (not shown) inside of a rigid shroud 330, posterior elastomeric damping element 331 and a single anterior elastomeric damping element 332, on the anterior portion of the offset shaft/pivot link vibration damping shroud(s) 333, and the anterior quick-connect housing connecting sleeve casing 335, all of which illustrated as encased in multiple adjoining vibration damping shrouds connecting to an anterior saw blade module 315.

Figure 10B:
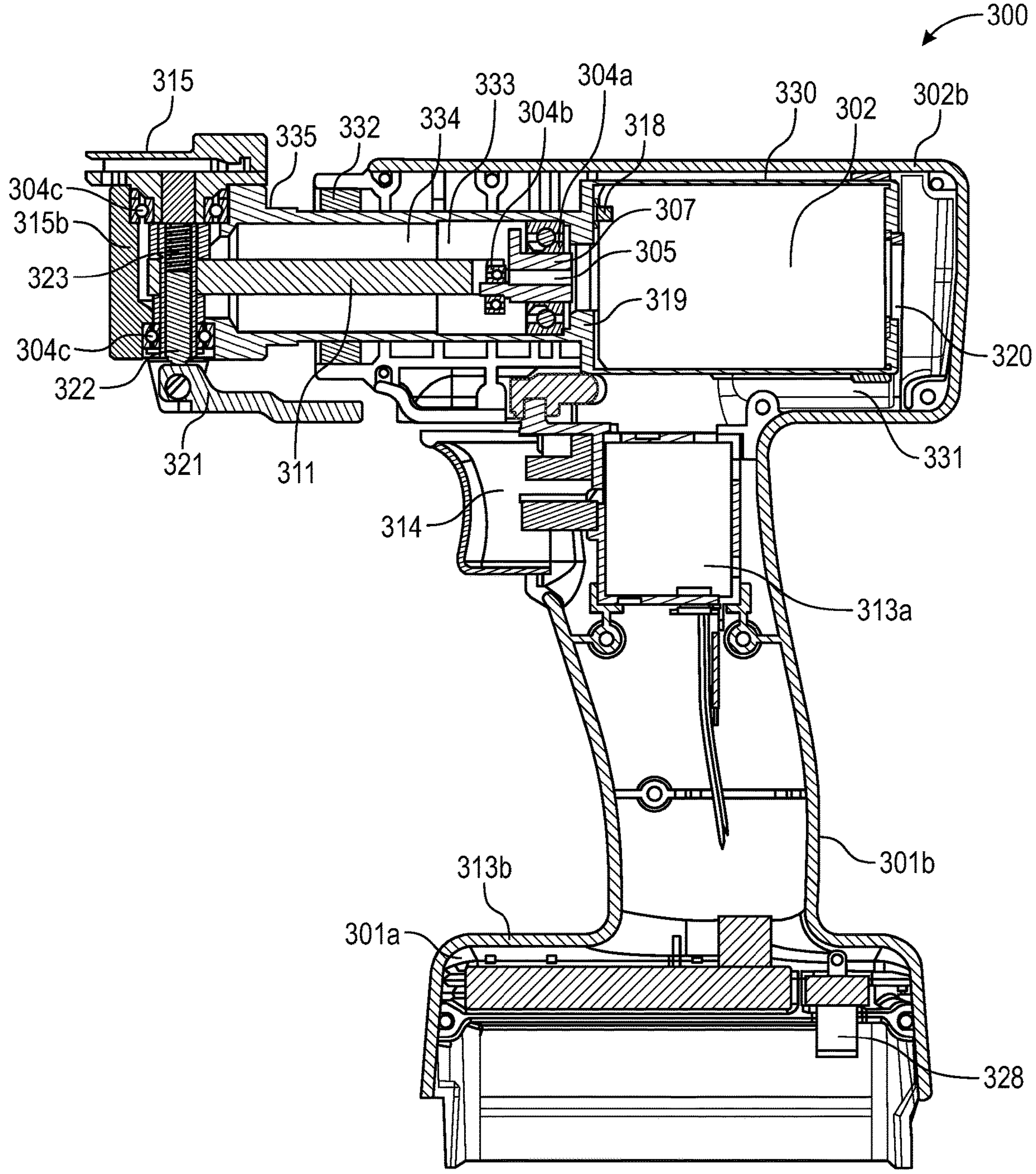
FIG. 10B is a further illustrative graphical representation of an orthogonal cut-away side section view of the entire saw body of FIG. 10A, illustrating another possible configuration of the modular internal drive components with an electro-mechanical drive motor, an offset shaft and an extended pivot link, all of which illustrated as encased in multiple adjoining vibration damping shrouds connecting to an anterior saw blade module; a speed control trigger and a trigger controller-processor and further illustrating a motor controller and partial section view of a battery compartment.

FIG. 10B is a further illustrative graphical representation of an cut-away side section view of the entire saw body 300 of FIG. 10A, illustrating another possible configuration of the modular internal drive components with an electro-mechanical drive motor 302, inside of a rigid shroud 330, posterior elastomeric damping element 331 and a single anterior elastomeric damping element 332, on the anterior portion of the offset shaft/pivot link vibration damping shroud(s) 333, mounting screws 318, front motor mount 319, an offset shaft 307 and an extended/long pivot link 311, all of which illustrated as encased in multiple adjoining vibration damping shrouds 330, 333, 334 connecting to an anterior saw blade module 315, via an anterior quick-connect housing connecting sleeve casing 335; a speed control trigger 314 and a trigger controller-processor 313*a* and further illustrating a motor controller 313*b* and partial section view of a battery compartment 301*a*, also showing a battery connector 328. Further still, inside of the anterior saw blade module housing 315*b*, one can see the sealed shaft bearings 304*c*, the pivot shaft 310, the blade lock compression spring 323 and the blade lock dowel pin 322.

Figure 10C:
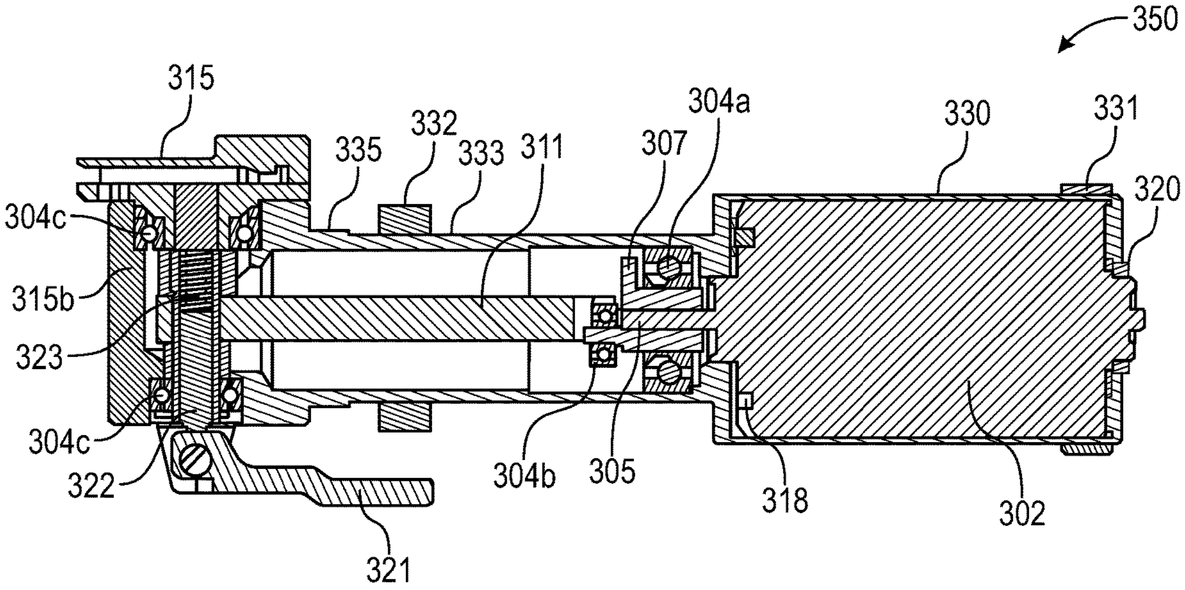
FIG. 10C is further illustrative representation of a cut-away side section view of the proximal body of FIG. 10B, illustrating a possible configuration of the modular internal drive components with an electro-mechanical drive motor, an offset shaft and an extended pivot link, all of which illustrated as encased in a single vibration damping shroud connecting to an anterior saw blade module; a speed control trigger and a trigger controller-processor and further illustrating a motor controller and partial section view of a battery.

FIG. 10C is further illustrative representation of a cut-away side section view of the proximal body of FIG. 10B, illustrating a possible configuration of a drive system cartridge 350 with an electro-mechanical drive motor 302, inside of an rigid shroud 330, posterior elastomeric damping element 331 and a single anterior elastomeric damping element 332, an offset shaft 307 and an extended pivot link anterior saw blade module 333, all of which illustrated as encased in a single vibration damping shroud 333, an anterior quick-connect housing connecting sleeve casing 335, connecting to an anterior saw blade module 315; and the internal components of the anterior saw blade module 315 described above.

Finally, the third embodiment illustrated in FIGS. 8, 9A, 9B, 10A, 10B and 10C, may further be described as a drive system cartridge 350 (which may be comprised of multiple components, i.e.: sub-casings or shrouds, (330, 333, 334, 335); containing the oscillating shaft or pivot link and fork 311, (with shaft support bearings 304*a*), the offset shaft 307, offset shaft (fork interface) bearing (304*b*) and drive motor 302. The individual bearings within the housing and motor may have damping elements (not shown) to isolate them from the drive system housing. The drive system cartridge itself 350, may be rigid or elastomeric and includes the sub-casings or shrouds, (330, 333, 334, 335) which may be comprised of elastomeric materials. The drive system cartridge has elastomeric mounting points (319, 320, 331, 332), to isolate it from the main housing which include the handle grip of the device. The mounting points may be circumferential, individual pads, threaded mounts, snap-fit mounts or comparable configurations.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A modular system comprising:

a limited-use battery-operated orthopedic hand tool having modular internal components; said modular internal components comprising:

a motor providing a rotational output;

an internal drive mechanism comprising: (1) a first motor output drive shaft; (2) a motor shaft coupling; (3) a second output shaft; and (4) at least one drive shaft bearing;

a first ring surrounding the at least one drive shaft bearing;

a second ring encircling the motor shaft coupling;

a third ring encircling the motor;

a handle grip;

a trigger mechanism to control the motor;

a control processor; and a battery;

wherein the first ring includes at least one of polychloroprene (neoprene), ethylene vinal acetate (EVA), polyvinyl chloride (PVC), or combinations thereof; the second ring includes at least one of neoprene, EVA, PVC, or combinations thereof; and the third ring includes at least one of neoprene, EVA, PVC, or combinations thereof.

2. The system of claim 1, further comprising a drive mechanism shroud encasing the internal drive mechanism.

3. The system of claim 2, wherein the drive mechanism shroud internally comprises one or more elastomeric dampers having a durometer between Shore A 60-100 or between Shore D 0-60.

4. The system of claim 2, wherein the drive mechanism shroud externally comprises one or more elastomeric dampers having a durometer between Shore A 60-100 or between Shore D 0-60.

5. The system of claim 1, further comprising:

a second drive shaft configured at a different orientation to the first motor output drive shaft;

at least one bearing on the second drive shaft; and an attachment receiver coupled to the second drive shaft for modular attachments used for performing surgical procedures;

wherein the second drive shaft and the at least one bearing on the second drive shaft further comprise elastomeric damping features.

6. The system of claim 5, wherein the internal drive mechanism comprises one or more elastomeric dampers having a durometer between Shore A 60-100 or between Shore D 0-60 about or around the first motor output drive shaft, the second output shaft, the second drive shaft, or combinations thereof.

7. The system of claim 5, wherein the attachment receiver is configured to receive cutting attachments.

8. The system of claim 5, further comprising a drive mechanism shroud encasing the internal drive mechanism, wherein the motor, the internal drive mechanism, the drive mechanism shroud, the trigger mechanism and the attachment receiver are configurable as modular components.

9. The system of claim 1, wherein the battery-operated orthopedic hand tool is:

a reciprocating saw; or an oscillating saw.

10. The system of claim 1, wherein the second output shaft is an offset shaft.

11. An oscillating saw system comprising:

a first housing;

a motor within the first housing;

a second housing;

a linkage;

a first shaft coupling the motor to the linkage, the first shaft including a central first axis that intersects the motor;

a second shaft coupled to the linkage, the second shaft having a central second axis that is orthogonal to the first axis;

a first bearing, wherein the second axis passes through the first bearing;

an elastomeric first ring surrounding the first bearing and directly contacting the first bearing;

an elastomeric second ring directly contacting the second housing and is inside the first housing but outside the second housing;

an elastomeric third ring encircling the motor;

wherein a first plane is orthogonal to the first axis and intersects the first and second housings;

wherein the elastomeric second ring is coplanar with the first plane;

wherein the elastomeric first ring includes at least one of polychloroprene (neoprene), ethylene vinal acetate (EVA), polyvinyl chloride (PVC), or combinations thereof;

wherein the elastomeric second ring includes at least one of neoprene, EVA, PVC, or combinations thereof;

wherein the elastomeric third ring includes at least one of neoprene, EVA, PVC, or combinations thereof;

wherein the oscillating saw is sterile.

12. The oscillating saw system of claim 11, wherein the first and second housings are separable from one another.

13. The oscillating saw system of claim 11, wherein the linkage is forked and includes opposing first and second tines.

14. The oscillating saw system of claim 13 comprising an offset shaft that couples the first shaft to the linkage.

15. The oscillating saw system of claim 14 comprising a sterile disposable packaging system, wherein the first and second housings are coupled to each other and are included in the sterile disposable packaging system.

16. The oscillating saw system of claim 11, wherein the motor is configurable to drive the second shaft between 7,000-14,000 oscillations per minute (OPM).

17. The oscillating saw system of claim 11 comprising a saw blade module configured to directly connect to a saw blade, wherein the central second axis intersects the saw blade module.

18. The oscillating saw system of claim 11 comprising a saw blade module configured to directly connect to a saw blade, wherein:

an additional axis is parallel to the central second axis;

the additional axis intersects the saw blade module.

* * * * *